United States Patent [19]
Laufer et al.

[11] Patent Number: 6,149,660
[45] Date of Patent: Nov. 21, 2000

[54] METHOD AND APPARATUS FOR DELIVERY OF AN APPLIANCE IN A VESSEL

[75] Inventors: Michael D. Laufer, Menlo Park; Gary H. Miller, Milpitas; Mark P. Parker, San Jose, all of Calif.

[73] Assignee: VNUS Medical Technologies, Inc., Sunnyvale, Calif.

[21] Appl. No.: 08/635,713

[22] Filed: Apr. 22, 1996

[51] Int. Cl.[7] ................................................. A61B 17/10
[52] U.S. Cl. ...................... 606/143; 606/139; 227/175.1
[58] Field of Search .................... 606/139, 142, 606/143; 227/175.1, 175.3, 177.1, 181.1

[56] References Cited

U.S. PATENT DOCUMENTS

| | | | |
|---|---|---|---|
| 2,817,339 | 12/1957 | Sullivan . | |
| 3,958,576 | 5/1976 | Komiya | 128/346 |
| 4,014,492 | 3/1977 | Rothfuss | 227/19 |
| 4,109,844 | 8/1978 | Becht | 227/120 |
| 4,179,057 | 12/1979 | Becht et al. | 227/19 |
| 4,256,251 | 3/1981 | Moshofsky | 227/120 |
| 4,261,244 | 4/1981 | Becht et al. | 411/472 |
| 4,287,890 | 9/1981 | Fogarty | 128/303 |
| 4,372,316 | 2/1983 | Blake, III et al. | 128/325 |
| 4,391,401 | 7/1983 | Moshofsky | 227/19 |
| 4,396,139 | 8/1983 | Hall et al. | 227/19 |
| 4,399,810 | 8/1983 | Samuels et al. | 128/337 |
| 4,505,273 | 3/1985 | Braun et al. | 128/335 |
| 4,621,636 | 11/1986 | Fogarty | 128/304 |
| 4,739,760 | 4/1988 | Chin et al. | 128/305 |
| 4,749,114 | 6/1988 | Green | 227/19 |
| 4,762,260 | 8/1988 | Richards et al. | 227/19 |
| 4,768,508 | 9/1988 | Chin et al. | 128/305 |
| 4,789,090 | 12/1988 | Blake, III | 227/19 |

(List continued on next page.)

FOREIGN PATENT DOCUMENTS

| | | | |
|---|---|---|---|
| 0 046 715 A2 | 3/1982 | European Pat. Off. . | |
| 085 930 A2 | 8/1983 | European Pat. Off. | A61B 17/08 |
| 0 094 752 A2 | 11/1983 | European Pat. Off. . | |
| 0 442 588 | 9/1985 | European Pat. Off. | A61B 17/068 |
| 0 229 453 A2 | 7/1987 | European Pat. Off. . | |
| 0 337 874 A1 | 10/1989 | European Pat. Off. . | |
| 337 874 A1 | 10/1989 | European Pat. Off. | A61B 17/10 |
| 0 386 361 A1 | 9/1990 | European Pat. Off. . | |
| 0 570 087 A 1 | 11/1993 | European Pat. Off. . | |
| 3204532 C2 | 8/1983 | Germany | A61B 17/08 |
| 3238892 A1 | 4/1984 | Germany | A61B 17/12 |
| 42 36 995 C 1 | 7/1993 | Germany | A61B 17/068 |
| 2 180 455 | 4/1987 | United Kingdom | A61B 17/10 |
| WO 89/04146 | 5/1989 | WIPO | A61B 17/08 |
| WO 91/10400 | 7/1991 | WIPO | A61B 17/00 |

Primary Examiner—Michael Buiz
Assistant Examiner—Lien Ngo
Attorney, Agent, or Firm—Fulwider Patton Lee & Utecht, LLP

[57] ABSTRACT

A delivery device and method for intraluminally deploying a clip appliance within a body lumen or cavity of a patient, for example a vein. The clip is configured from a wire-like, bendable material, having a "W"-like sinusoidal shape. The clip is constructed with sharpened slanted edges at the tips which provide preferential bending and straightening when the clip is deployed into patient tissue, for example, a venous valve. The delivery device comprises a catheter and a structure for bending and releasing the clip. The catheter is configured with an elongate flexible tubular member secured to a slotted housing having a distal tapered tip. A handle is secured to the proximal end of the flexible tubular member. A balloon and actuator arm combination is disclosed for forcing a clip against an anvil to bend the clip from an open to a closed condition and for releasing the clip from a slot in a side wall of the housing. The housing may be configured to retain and deploy a plurality of clip appliances. During clip deployment, the catheter housing is positioned within a vessel or viscus of a patient, and the slot in the side wall is precisely aligned and stabilized with a second inflatable member. A force is applied to the clip to bend the clip and secure it to the desired location and the clip is released from the delivery device through the slot in the housing.

114 Claims, 19 Drawing Sheets

U.S. PATENT DOCUMENTS

| | | |
|---|---|---|
| 4,809,695 | 3/1989 | Gwathmey et al. . |
| 4,872,874 | 10/1989 | Taheri et al. ............................... 623/1 |
| 4,899,745 | 2/1990 | Laboureau et al. . |
| 4,904,254 | 2/1990 | Lane ............................................ 623/2 |
| 4,915,107 | 4/1990 | Rebuffat et al. ........................ 606/144 |
| 4,969,591 | 11/1990 | Richards et al. ........................ 227/177 |
| 5,042,707 | 8/1991 | Taheri . |
| 5,129,570 | 7/1992 | Schulze et al. ........................... 227/19 |
| 5,156,609 | 10/1992 | Nakao et al. ............................ 606/142 |
| 5,219,111 | 6/1993 | Bilotti ..................................... 227/175 |
| 5,242,457 | 9/1993 | Akopov .................................... 606/144 |
| 5,258,009 | 11/1993 | Conners . |
| 5,297,714 | 3/1994 | Kramer .................................... 227/175 |
| 5,300,033 | 4/1994 | Miller ....................................... 604/167 |
| 5,304,184 | 4/1994 | Hathaway et al. ...................... 606/144 |
| 5,330,488 | 7/1994 | Goldrath ................................. 606/148 |
| 5,342,376 | 8/1994 | Ruff ......................................... 606/151 |
| 5,411,552 | 5/1995 | Andersen et al. ........................... 623/2 |
| 5,413,584 | 5/1995 | Schulze ................................... 606/219 |
| 5,413,599 | 5/1995 | Imachi et al. ............................... 623/2 |
| 5,439,468 | 8/1995 | Schulze et al. ......................... 606/143 |
| 5,465,896 | 11/1995 | Allen et al. ............................. 227/176 |
| 5,484,095 | 1/1996 | Green et al. .......................... 227/181.1 |
| 5,618,311 | 4/1997 | Gryskiewicz ........................... 606/216 |
| 5,704,534 | 1/1998 | Huitema et al. ..................... 227/175.1 |

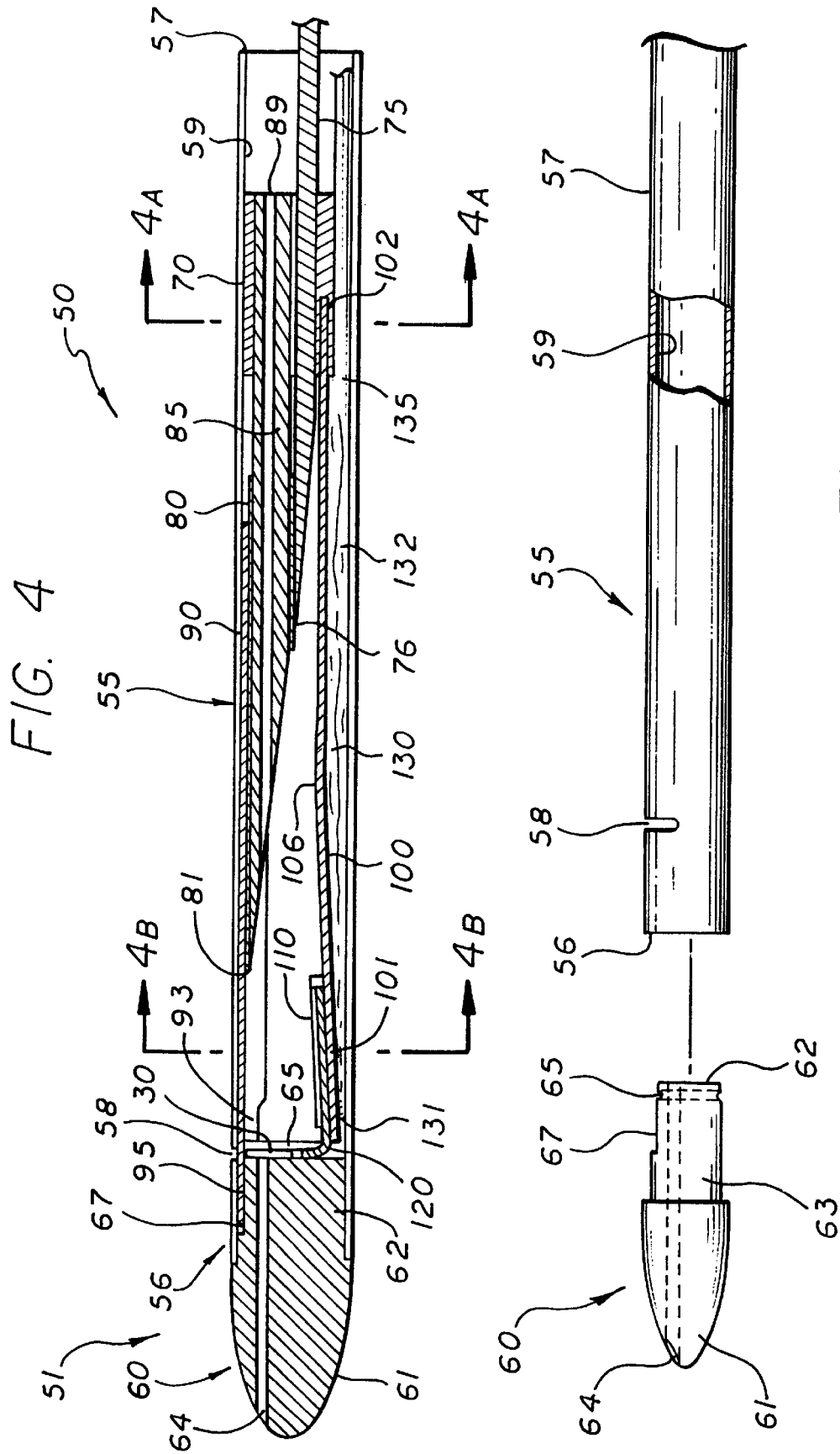

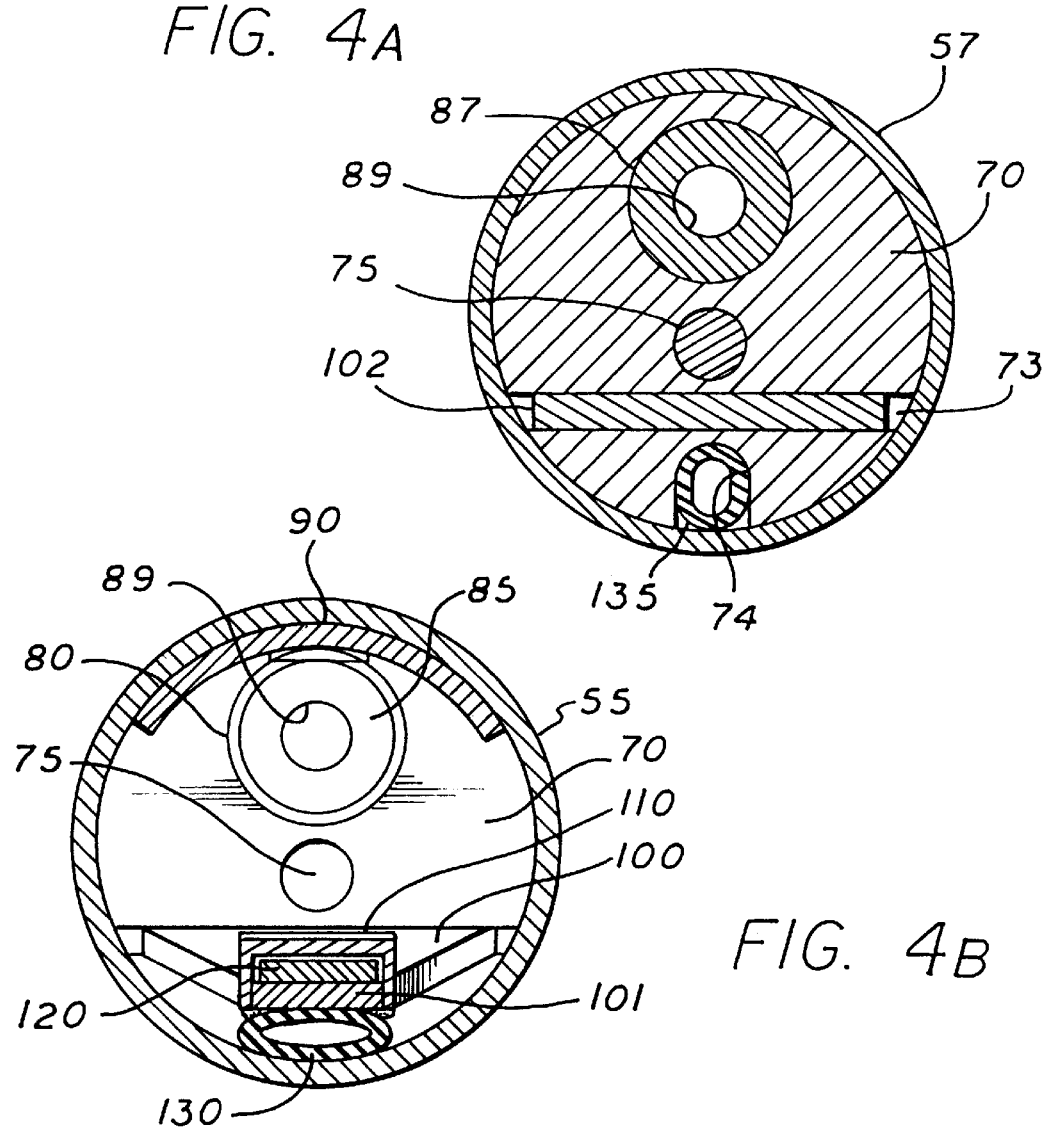
FIG. 4A
FIG. 4B
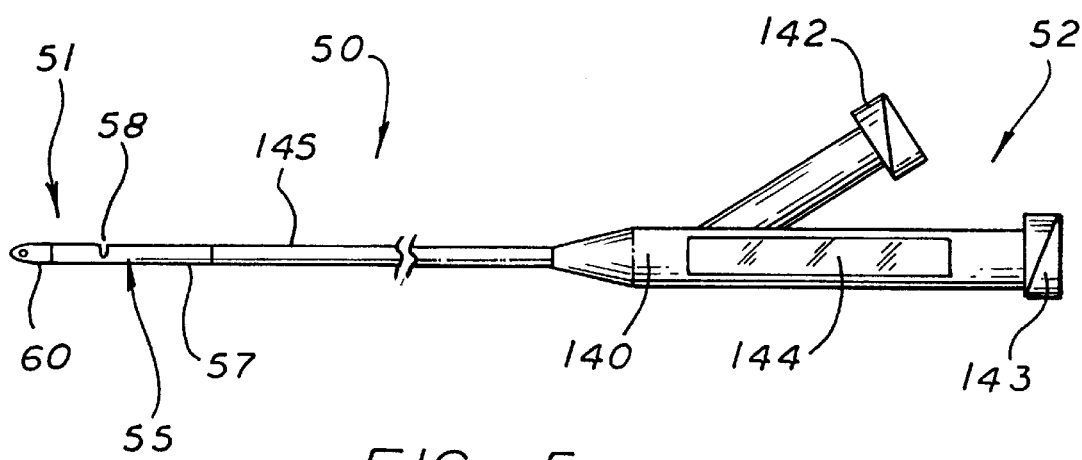
FIG. 5

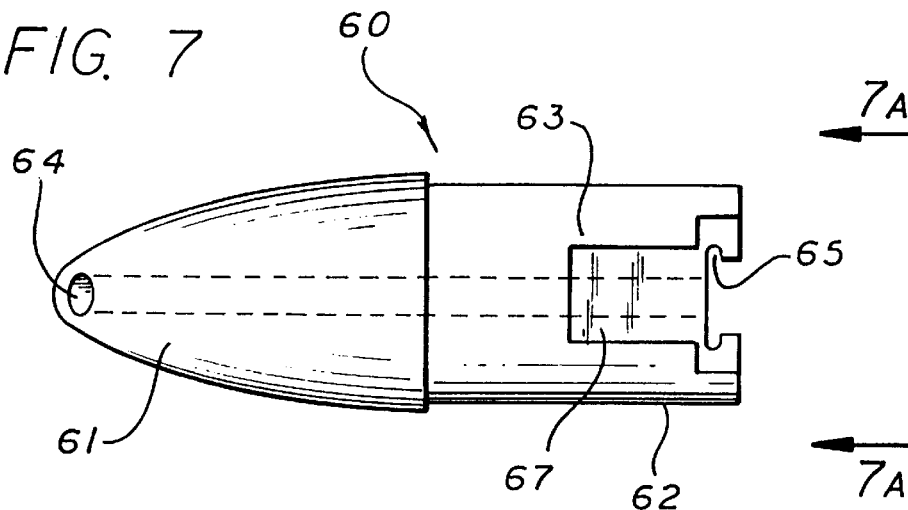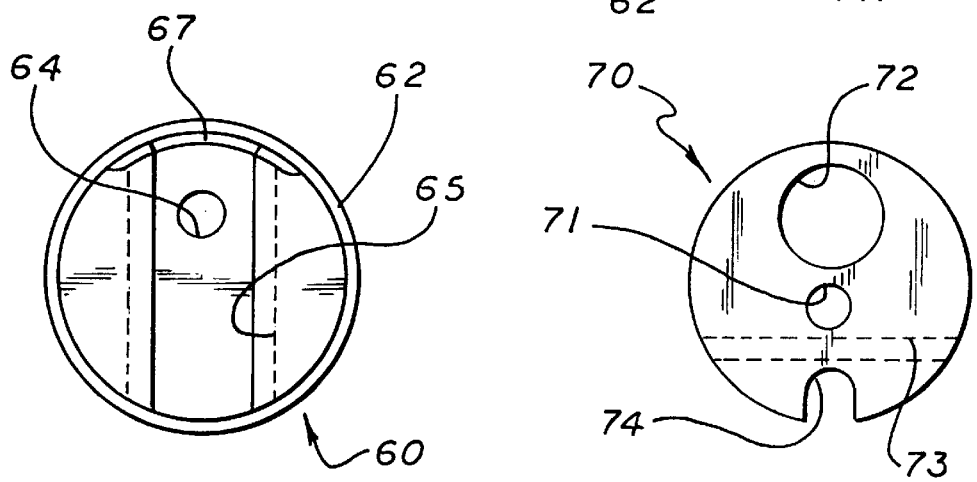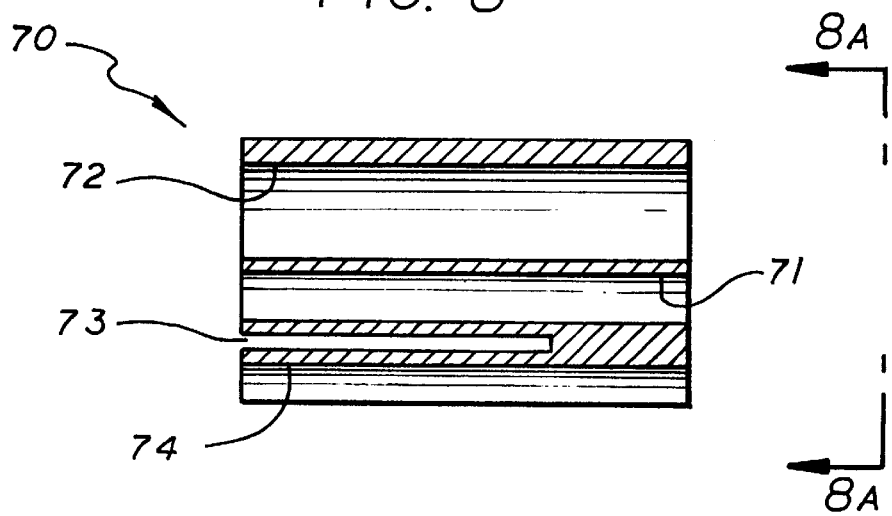

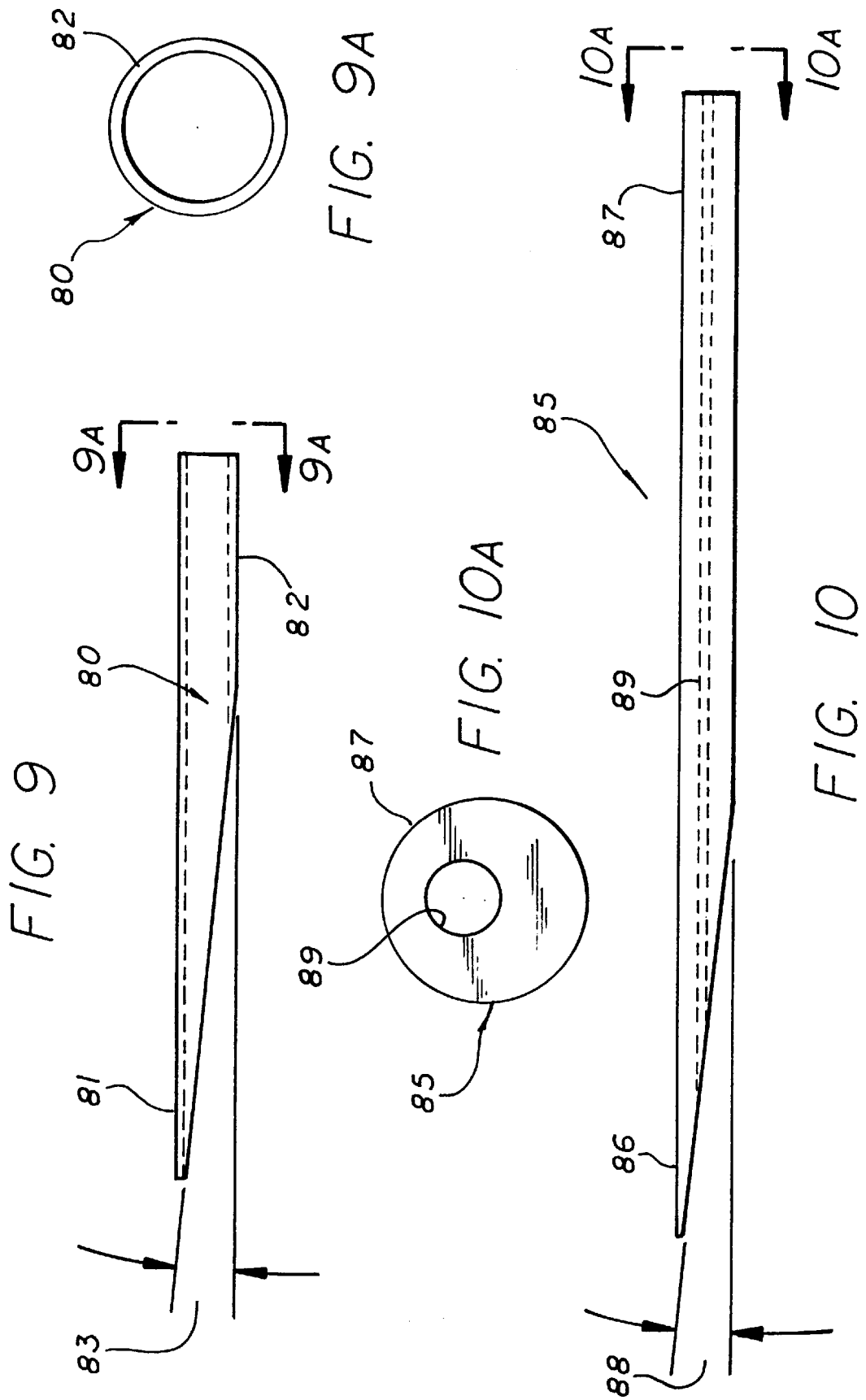

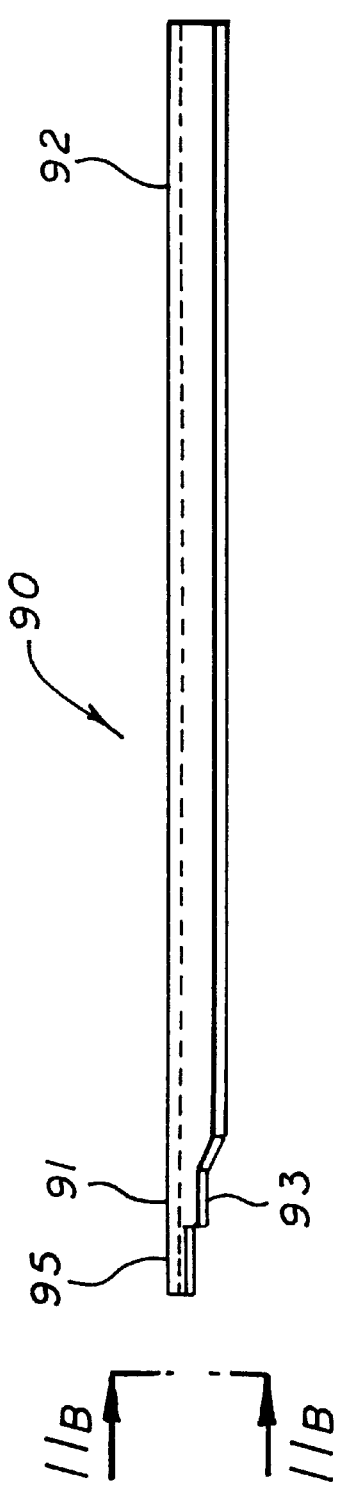
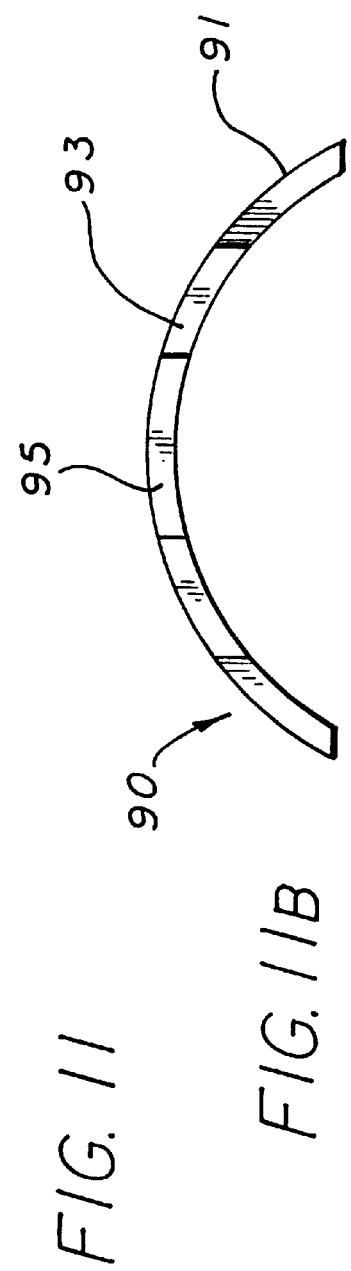
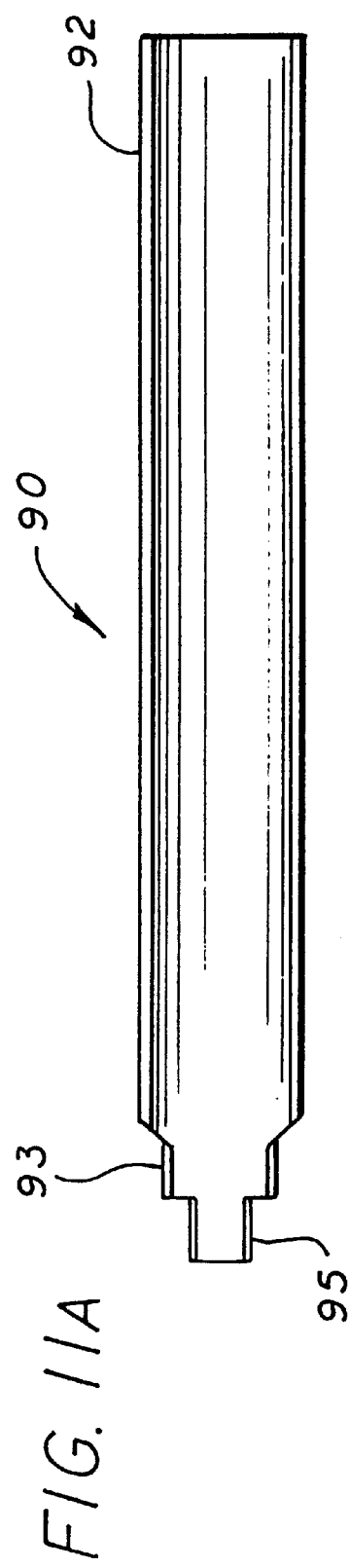
FIG. 11
FIG. 11B
FIG. 11A

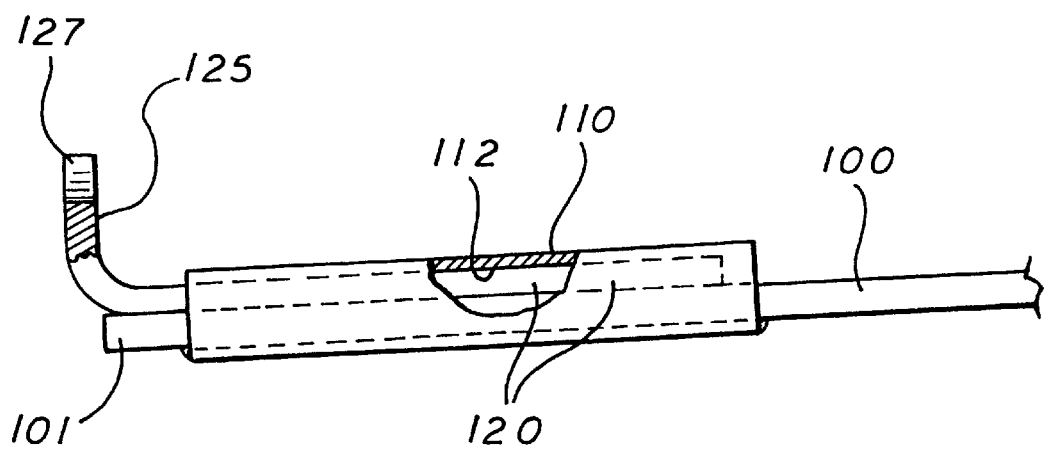
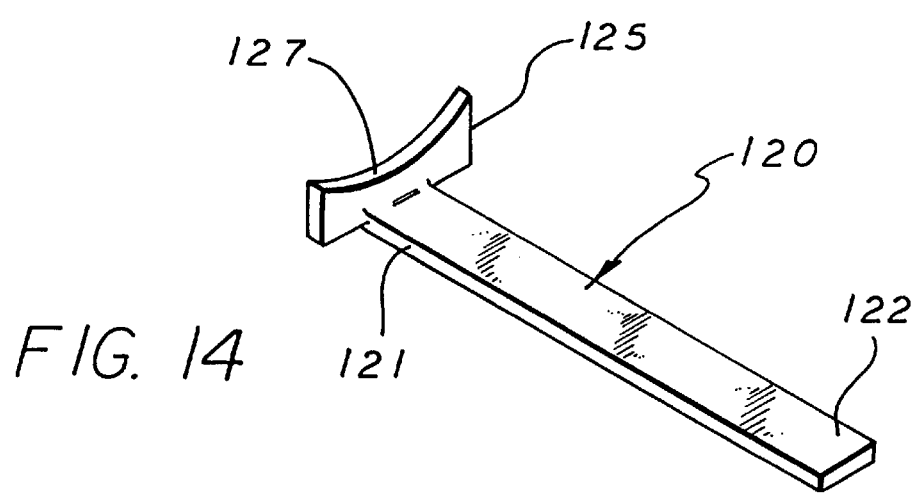
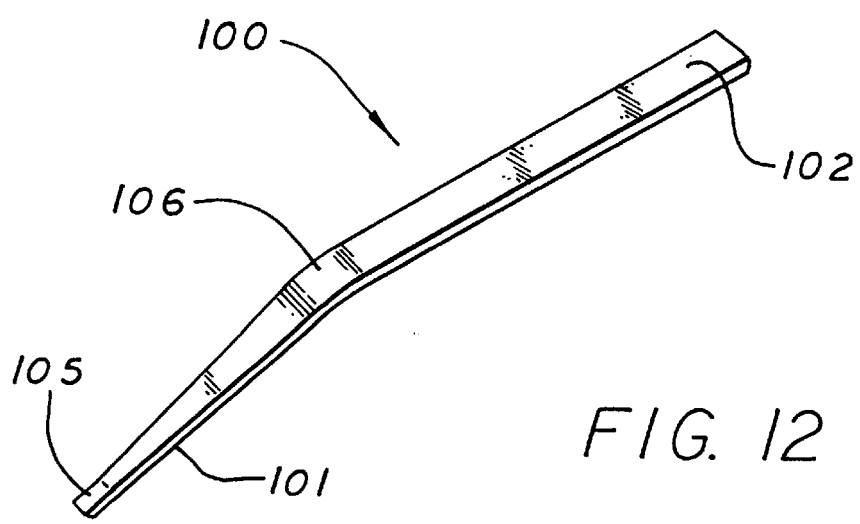

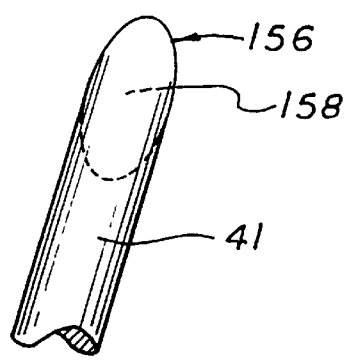
FIG. 23A
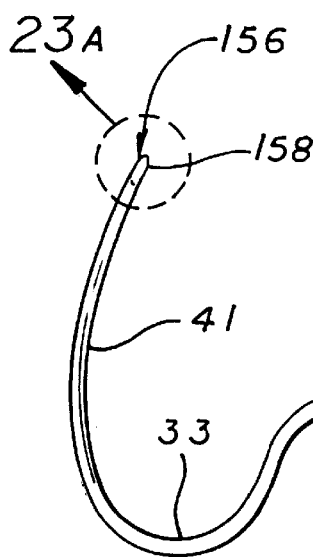
FIG. 23
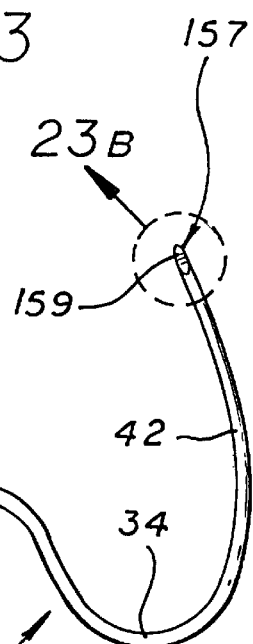
FIG. 23B
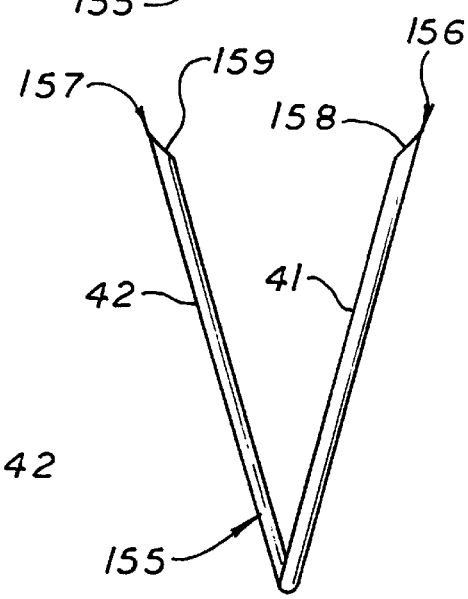
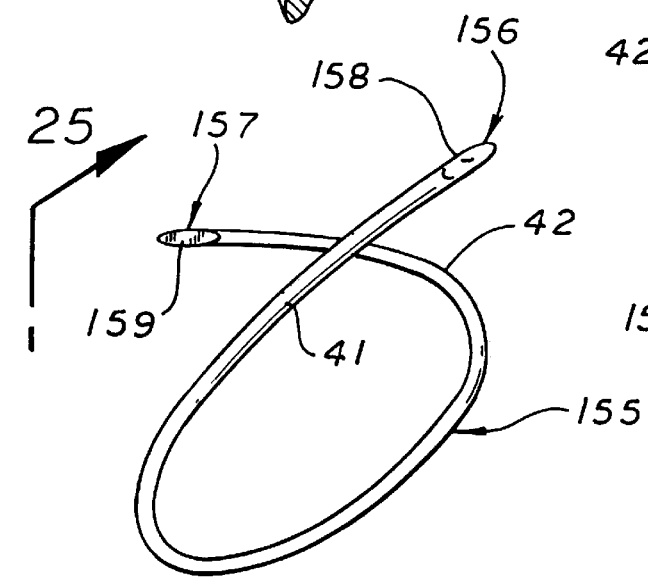
FIG. 24
FIG. 25
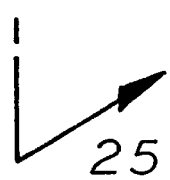

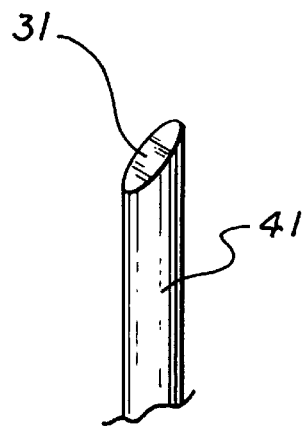
FIG. 26
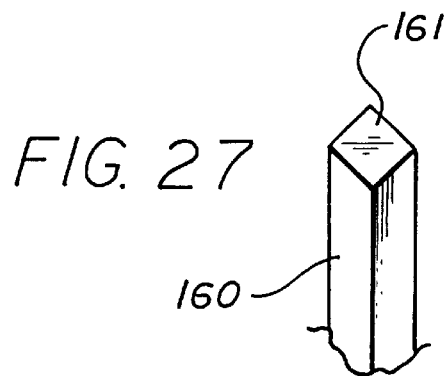
FIG. 27
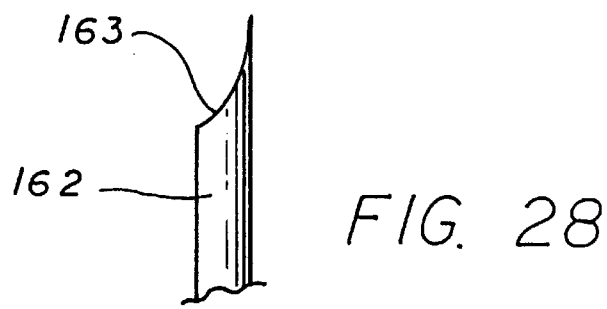
FIG. 28
FIG. 29
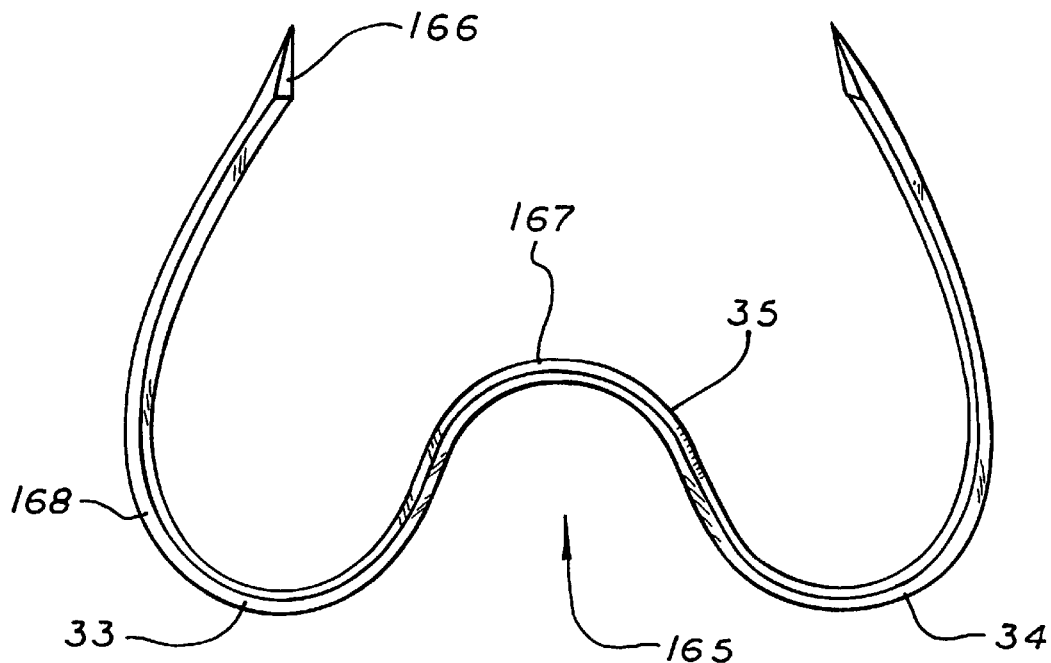

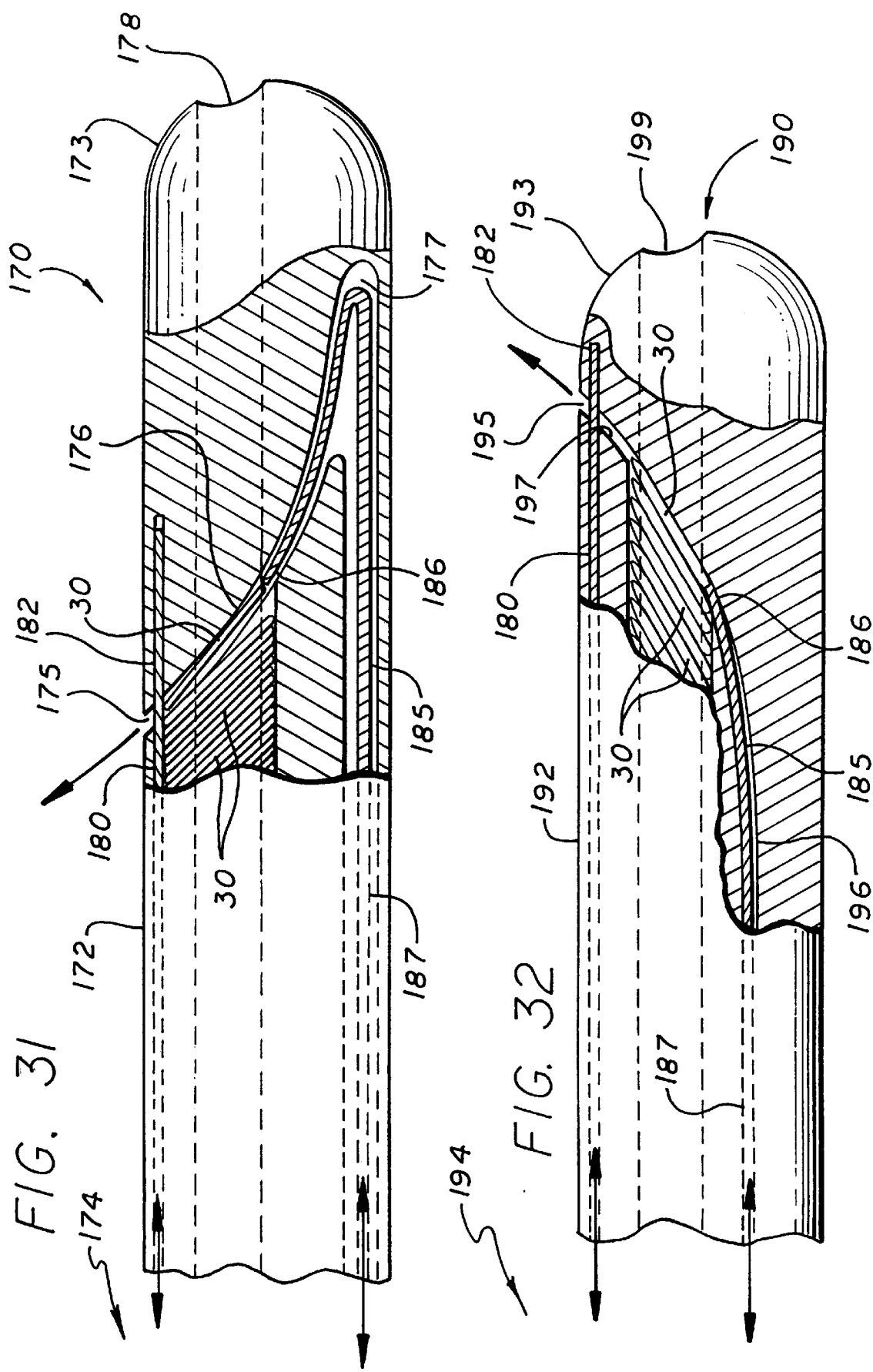

METHOD AND APPARATUS FOR DELIVERY OF AN APPLIANCE IN A VESSEL

BACKGROUND OF THE INVENTION

This invention relates to the repair of a hollow viscus organ or vessel using a catheter based system to deploy an appliance, such as a bendable clip, and more particularly to minimally invasive correction of venous insufficiency for correction of incompetent venous valves.

An unresolved need exists for the repair of certain incompetent or damaged human body components, such as certain viscous organs, body lumens and cavities, for example, a damaged blood vessel or an incompetent vein valve. More particularly, chronic venous insufficiency is a problem caused by hydrodynamic forces acting on the lowest part of the body, the legs, ankles and feet. As the veins dilate due to increased pressure, the valves in the veins become less able to withstand the weight of the blood above them. This causes the veins to dilate further and the valves in the veins to fail, i.e., become incompetent. Venous valves are typically bicuspid valves, with each cusp forming a sack or reservoir for blood which, under pressure, forces the free edges of the cusps together to prevent retrograde flow of the blood and allow only antegrade flow to the heart. When an incompetent valve attempts to close in response to a pressure gradient across the valve, the cusps do not seal properly and retrograde flow of blood occurs.

Incompetence in the venous system can result from vein dilation, which causes the veins to swell with additional blood. Separation of the cusps of the venous valve at the commissure may occur as a result. The leaflets are stretched by the dilation of the vein and concomitant increase in the vein diameter which the leaflets traverse. Stretching of the leaflets of the venous valve results in redundancy which allows the leaflets to fold on themselves and leave the valve open. This is called prolapse, which can allow reflux of blood in the vein. Eventually the venous valve fails, thereby increasing the strain and pressure on the lower venous sections and overlying tissues.

Chronic venous insufficiency consists of venous hypertension of the lower limb in the deep, perforating and often superficial veins with associated pigmentation, pain, swelling and ulceration. Existing treatments for chronic venous insufficiency are less than ideal. The only known therapies currently available include elevation of the legs for extended periods, elastic support hose to compress the veins externally and surgical repair or replacement of the vein and valves. These methods are variably effective. In addition, a physician has no efficacious drugs at his disposal, and the surgeon does not have ready access to artificial venous valves. Moreover, the use of reconstructive surgery is impeded by the delicate nature and irreversible damage of the valvular structures.

Prior known prostheses include artificial venous valves and artificial valves for the heart and other anatomy which are adaptable for use in a vein. One such disclosed venous valve is comprised of an annular support member or ring defining an opening therethrough, including leaflets hingedly attached to the support ring for opening and closing the support ring opening in a manner permitting substantially unidirectional flow therethrough. Such valves are designed to be sutured or sewn into place within a blood vessel during a lengthy open surgery.

Also known is a cuff for restoring competence to an incompetent venous valve which consists of a band of biocompatible implantable material that is not stretchable at blood flow pressures. The band is of sufficient length to encompass a vein at the sight of a vein valve with the ends of the band overlapping. In one form of attachment, a first end of the band passes over a loop in a second end and is stapled thereto. The cuff is placed around a vein at the site of the incompetent valve and the diameter of the vein at the valve site is reduced until competency of the vein valve is restored.

Certain conventional surgical endoscopic, and laparoscopic procedures utilize staples or clips for repair of incisions or wounds, implantation of prostheses, anastomoses and the like. For example, surgical staples have been disclosed comprising angled and arcuate central and leg regions which can be flattened by a stapling tool having an anvil and driving structure. One such staple has been disclosed with side portions curved substantially in the form of an arc of a circle to prevent tearing of tissue by producing puncture channels.

Various forms of stapling tools also have been disclosed. One such surgical instrument consists of an anvil adapted to lie flush with the skin, a cartridge containing a plurality of staples and a U-shaped pusher for bending the staples around the anvil. Such instruments typically have mechanical actuators within a handle mechanism for positioning the staples and activating the driver or pusher against the staple and anvil.

Laparoscopic procedures have also used staples, balloons and clip appliers or staple guns for procedures such as cholecystostomies, ligation and hernia repair. Such systems have heretofore not been known to be disclosed for intraluminally repairing blood vessels or vein valves. Such limitations apparently are the result of clip and applier design. Thus, there is a need for a minimally invasive system for intraluminal repair of a body organ, lumen or cavity, for example, a blood vessel or a vein valve, using a catheter based system for deploying a bendable clip appliance.

To provide consistency with the common usage of terms used in the medical surgical arts in the United States, the terms "proximal and distal" are used with a certain meaning within the present specification. "Proximal" refers to a location of an element of the apparatus, such as a catheter, housing or wire, which is closest to the user (physician) and closest to the portion of the apparatus outside or exterior of the patient. Similarly, for the catheter elements, "distal" refers to the point farthest from the user and typically most interior to the body or lumen. With blood vessels and venous valves, "proximal" refers to a portion closest to the heart, and "distal" refers to a portion furthest from the heart.

SUMMARY OF THE INVENTION

Briefly, and in general terms, the invention provides a delivery device and method for applying a clip appliance to a vein or other body lumen or cavity of a patient. The clip is configured from a wire-like, bendable material, having a "W" or sinusoidal shape prior to deployment from the delivery device. Upon delivery, the clip is bent so as to be secured to the tissue of the patient. The delivery device comprises a catheter having a housing at its distal portion for retaining and deploying the clip. A biasing apparatus, such as an actuator arm and balloon, is used to force the clip against an anvil to bend the clip during deployment into a vein valve or other suitable body part to be repaired.

The clip of the present invention is configured for intraluminal delivery from an elongate body formed from a bendable material, such as stainless steel. The clip preferably is formed with a first leg having a first end, a second leg having a second end, a first arcuate portion configured in the first leg, a second arcuate portion configured in the second leg; and a third arcuate portion configured between the first arcuate portion and the second arcuate portion. The shape formed by the legs and arcuate portions is sinusoidal or "W"-like. The clip is constructed in a manner that provides preferential bending and straightening at the third arcuate portion when the clip is deployed into patient tissue, for example, a vein valve.

The shape and sharpening of the wire of the clip has several variations. The clip may be made from a substantially round wire, such that the first and second ends are each formed to a sharp slanted edge. Alternatively, the clip is made from a three-sided, four-sided or other suitably shaped wire or other bendable material. The ends of the legs may be sharpened to form slanted edges directed toward or away from each other. Similarly, each slanted edge may be directed ninety degrees from the plane of the clip and about one hundred eighty degrees from each other. Such configurations of the slanted edges provide for deployment of the clip so that the first leg bends away from and out of the plane of the clip and the second leg bends away from the plane of the clip and away from the first leg.

The delivery device of the present invention includes a catheter for intraluminally deploying a clip appliance, for example, a "W"-shaped clip as described heretofore. The catheter comprises a housing having a distal end, a proximal end and a side wall having a slot for deploying a clip. The delivery device further includes structure for deploying a clip or a plurality of clips through the slot in the housing. The housing may further be configured with a diverting balloon configured on the side wall.

The catheter preferably includes a flexible portion secured to a housing formed from a rigid material and secured to a distal tapered tip. In addition, a handle may be secured to a proximal end of the flexible portion. Also, the catheter may be configured with a lumen extending through the flexible portion and the housing. The lumen is connected to an access port in the handle and has a distal opening near the distal end of the tapered tip. The lumen is configured for a guidewire or introducer needle to be slidably disposed therein, such that the guidewire or needle locks or releasably retains the clip within the housing.

The delivery device further includes structure for bending a clip from an open to a closed condition and releasing the clip from the housing. A retainer arm is slidably disposed within the housing, having a distal end configured with an anvil formed to bend the clip. A slide wire may be secured to the retainer arm and slidably disposed within the catheter. Proximal longitudinal movement of the slide wire moves the retainer arm from a position which prevents the clip from releasing through the eject slot to a position where the clip may engage the anvil.

Disclosed herein are several alternative structures for forcing the clip against the anvil for bending the clip into a vein valve or similar patient body part. For example, an inflatable member, such as a balloon, configured to engage an actuator arm may be used to engage a clip. Similarly, a force arm, force wedge or force wire may be used to drive the clip against the anvil, through the eject slot and into the patient. A floating actuator tip may be configured on the distal end of the actuator arm or force arm to maximize penetration of the clip legs, to enhance straightening of the clip middle arcuate portion, and to maximize crossing of the clip legs.

The method of the present invention uses the delivery catheter to deploy a clip into a body organ, lumen or cavity, for example, a blood vessel or a vein valve, or other suitable patient body part to be repaired or treated. To begin the procedure, a distal portion of a catheter comprising a housing having a clip eject slot is inserted into a patient. The housing is positioned at a desired location in the patient, and the clip eject slot is precisely aligned for clip deployment. The clip is then manipulated within the housing to position the clip proximate the eject slot. A force is applied to the clip to secure the clip to the desired location in a patient and the clip is released from the housing through the eject slot. Lastly, the catheter is removed from the patient.

The clip may be bent and secured to the patient by using any of the several structures of the present invention.

In addition, several clips may be deployed longitudinally within the cavity or lumen, for example, along the commissure of a vein valve. Likewise, clips may be deployed on each commissure of a single or of multiple vein valves. A diverting balloon is used to move the eject slot in close proximity to a particular location, for example a wall of the vein valve.

The system of the present invention is a significant advancement in minimally invasive surgical procedures. More particularly, the system provides a much less painful, less expensive and faster method for solving the underlying problems of venous valve insufficiency than the current conventional systems. The apparatus and method of the invention eliminate the need for open surgical valve repair procedures, obviate the need for arm vein transplantation into the leg, and allow patients to return to their former active lifestyles without the limitations currently associated with the treatment of the condition.

During a vein valve repair procedure, a delivery catheter containing one or a plurality of clips is placed into the vein to be repaired. The delivery device is moved within the vein toward the heart and is positioned at the level of the first incompetent valve to be repaired. A clip appliance is deployed from the catheter and affixed to the valve. More than one clip may be secured on the same or either commissure. After the clip is secured in place, the distal end of the delivery device is positioned proximate the next venous valve to be repaired. All incompetent valves may be repaired, or specific valves may be repaired.

This invention also provides a physician or surgeon the capability to repair structures from within a vessel lumen, body cavity or viscus with clips in a way which is not currently available. The catheter allows entry into various body areas such as a vein, and allows the surgeon or physician the opportunity to perform such procedures without the current need to open the blood vessel and overlying muscle, fascia and skin. Such procedures utilizing the apparatus and method of the present invention may result in shorter hospital stays, fewer operative complications and a better overall result for the patient.

In such use for repairing a viscus, a patient may have the delivery catheter of the present invention placed through an introducer similar to that used in well known colonoscopy procedures, from the anus to the area of the appendix. For example, the appendix would then be isolated and the catheter would be used to clip the connection between the small intestine and appendix. Thus, the physician may perform an appendectomy from within the intestine without the need for general anesthesia, and without the need for a surgical incision or its concomitant scarring or adhesion predilection. This method has benefits over current laporascopic approaches in that it is even less invasive than "minimally invasive" surgery.

These and other features and advantages of the present invention will become apparent from the following more detailed description, when taken in conjunction with the accompanying drawings which illustrate, by way of example, the principles of the invention.

BRIEF DESCRIPTION OF THE DRAWINGS

FIG. 4 is a side elevational view in cross-section of the delivery device of the present invention for positioning and securing the clip of FIG. 3.

FIG. 4A is a cross-sectional view taken along the line 4A—4A of FIG. 4.

FIG. 4B is a cross-sectional view taken along the line 4B—4B of FIG. 4.

FIG. 5 is a side elevational view of the delivery device of the present invention showing the proximal portion of the device.

FIG. 6 is a side elevational view in partial cross-section of the distal portion of delivery device in FIG. 4, showing the tapered tip detached from the slotted housing.

FIG. 7 is a top plan view of the tapered tip of the delivery device shown in FIG. 4.

FIG. 7A is an end elevational view of the tapered tip shown in FIG. 7.

FIG. 8 is a side elevational view in cross-section of the slotted housing plug of the delivery device of FIG. 4.

FIG. 8A is an end elevational view of the slotted housing plug shown in FIG. 8.

FIG. 9 is a side elevational view of the anvil slide tube of the delivery device of FIG. 4.

FIG. 9A is an end elevational view of the anvil slide tube shown in FIG. 9.

FIG. 10 is a side elevational view of the anvil guiding tube of the delivery device of FIG. 4.

FIG. 10A is an end elevational view of the anvil guiding tube shown in FIG. 10.

FIG. 11 is a side elevational view of the retainer arm and anvil of the delivery device of FIG. 4.

FIG. 11A is a bottom elevational view of the retainer arm and anvil shown in FIG. 11.

FIG. 11B is a distal end elevational view of the retainer and anvil shown in FIG. 11.

FIG. 12 is a perspective view of the actuator arm of the delivery device of FIG. 4.

FIG. 13 is a side elevational view of the floating tip retainer assembly of the delivery device of FIG. 4.

FIG. 14 is a perspective view of the floating actuator tip of the delivery device of FIG. 4.

FIG. 23 is a top plan view of an embodiment of the clip appliance of the present invention showing an alternative configuration of the slanted edges of the clip.

FIG. 23A is an enlarged plan view of the first slanted edge of the clip of FIG. 23.

FIG. 23B is an enlarged plan view of the second slanted edge of the clip of FIG. 23.

FIG. 24 is a perspective view of the clip of FIG. 23 after the clip has been bent and deployed from the delivery device.

FIG. 25 is an end elevational view of the clip of FIG. 24.

FIG. 26 is an enlarged perspective view of the distal tip and slanted edge of the first leg of the clip of FIG. 3 formed from a round wire.

FIG. 27 is an enlarged side elevational view of the distal tip and slanted edge of an alternative embodiment of a leg of a clip of the present invention formed from a rectangular wire.

FIG. 28 is an enlarged side elevational view of the distal tip and slanted edge of an alternative embodiment of a leg of a clip of the present invention formed from a round wire, wherein the slanted edge is shaped into a sharp arcuate angle.

FIG. 29 is a top plan view of an alternative embodiment of the clip appliance of the present invention formed from a triangular wire and having slanted edges out of the plane of the clip.

FIG. 31 is a side elevational view in partial cross-section of an alternative embodiment of the delivery device of the present invention comprising a pull force wire and clip bundle.

FIG. 32 is a side elevational view in partial cross-section of an alternative embodiment of the delivery device of the present invention comprising a push force wire and clip bundle.

DETAILED DESCRIPTION OF THE PREFERRED EMBODIMENTS

Figure 1:
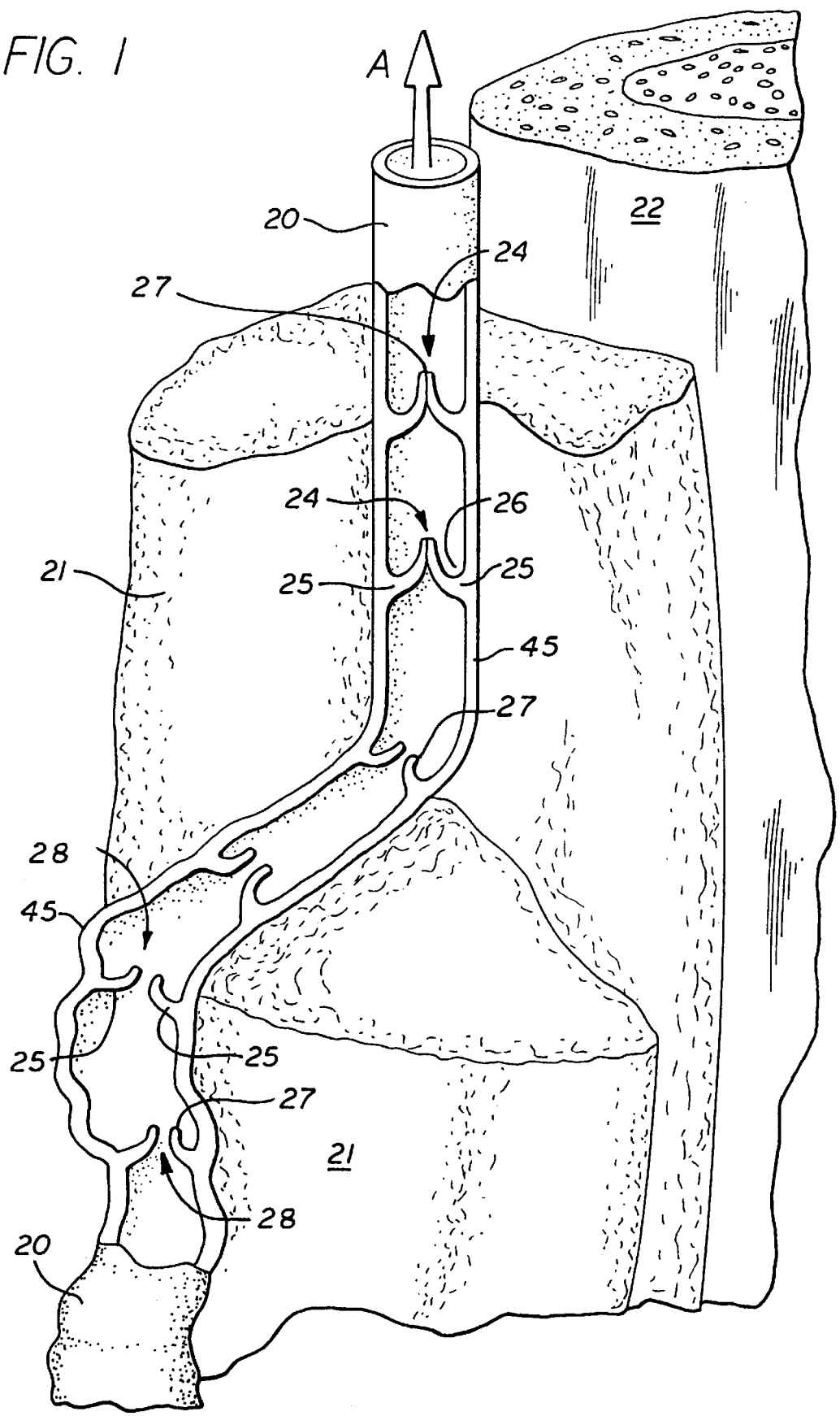
FIG. 1 shows a perspective view in partial cross-section of a vein having both competent and incompetent valves.

As shown in the exemplary drawings, the invention is embodied in a clip appliance 30 and delivery device or delivery catheter 50 for use in a vein 20 or other body lumen or cavity of a patient. For illustrative purposes, the delivery device and clip of the present invention is described for minimally invasive treatment of chronic venous insufficiency. As shown in FIG. 1, venous valves are usually bicuspid valves and are disposed within muscle tissue 21 and may be deep near a bone 22. In a normal and competent valve 24, each leaflet 25 forms a sack or reservoir 26 for blood which, under pressure, forces the free edges or cornu 27 of the leaflets together to prevent retrograde flow of the blood and allow only antegrade flow to the heart (Arrow A). When an incompetent valve 28 attempts to close in response to flow across the valve, the cornu of the leaflets do not seal properly and retrograde flow of blood occurs.

In accordance with the present invention, a clip 30 is positioned by the delivery catheter 50 within the vein 20 adjacent an incompetent valve 28. The catheter is used to position and deploy a clip into a vein wall 45 so as to adjust the leaflets 25 of the venous valve to return the valve to its normal and competent function. Thus, the device and method of the invention eliminate the need for open surgical valve repair procedures, such as vein transplantation into the leg, and allow patients to return to their former active lifestyles without the limitations currently associated with the treatment of chronic venous insufficiency.

Figure 2:
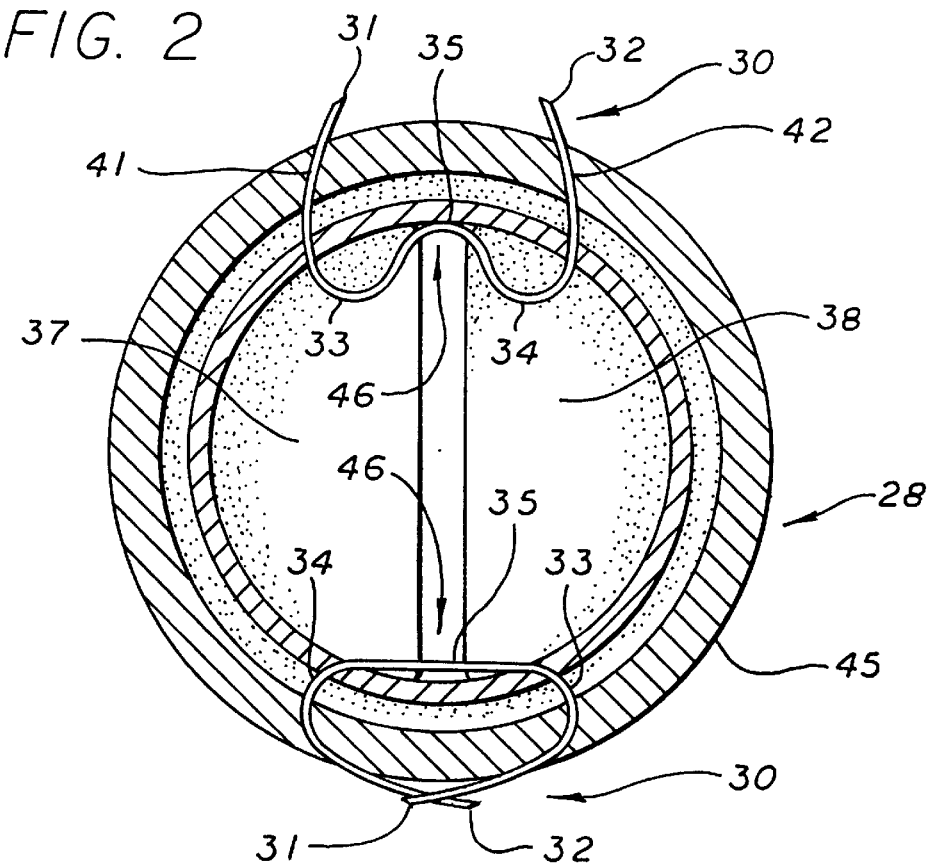
FIG. 2 is a top plan view in partial cross-section of two clip appliances of the present invention secured within the commissure of a valve within a vein.

As shown in FIG. 2, the clip appliance 30 is staple-like having a "W" shape and configured to pierce a body member, for example, a viscus organ, a blood vessel or an incompetent vein valve 28. The clip is constructed so that it will fit within a distal end of a delivery device. The clip is configured from a bendable wire-like material with sharp spreadable legs 41, 42 so as to fit over both sides of the venous valve. The clip is further configured to close by compression so as to pinch the tissue of the viscus or vessel together, e.g., lock the legs over a venous valve and through the vein. The clip appliance is made of a bendable biocompatible material, such as a polymer, metal or fabric, and preferably of #420 stainless steel.

As further shown in FIG. 2, the clip 30 is deployed within the commissure of a valve 28 in a vein. The first arcuate portion 33 is placed adjacent to a first leaflet 37 of the valve 28. Similarly, the second arcuate portion 34 is placed proximate the other valve leaflet 38, and the third arcuate portion 35 is positioned within the commissure. Force is applied to the clip to pierce the legs 31 and 32 through both valve leaflets and through the vessel wall 45. The first and second ends of the clip protrude through the vessel wall while the middle arcuate portion remains within the vein lumen.

Figure 3:
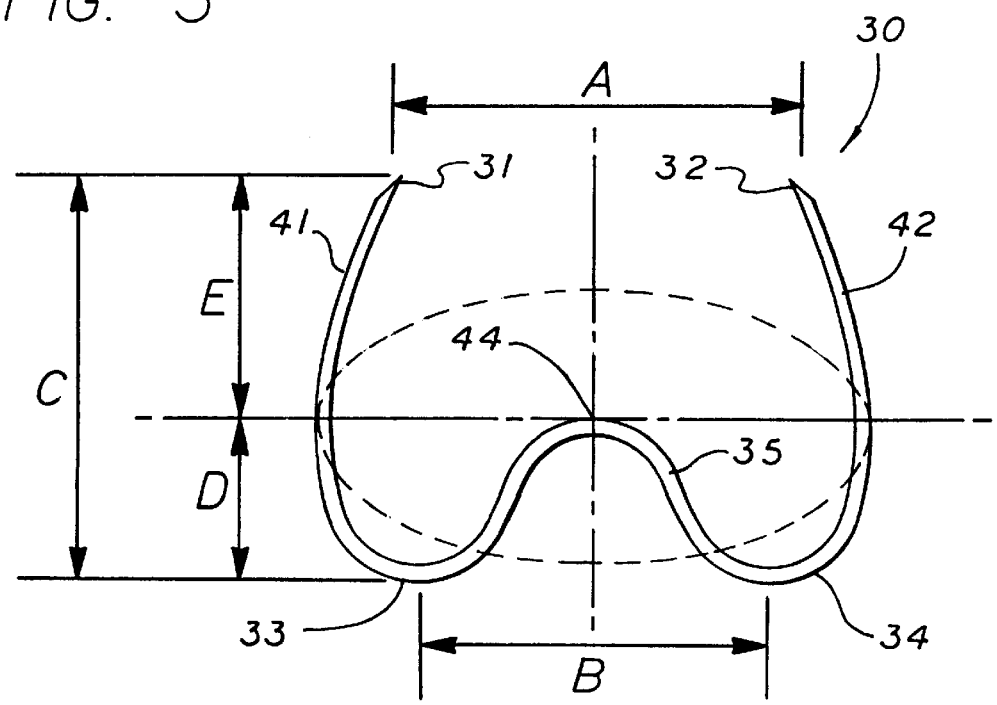
FIG. 3 is a top plan view of the clip appliance of the present invention showing certain dimensions thereof.

Referring to FIG. 3, the clip 30 of the present invention is configured for intraluminal delivery from an elongate body formed from a bendable material, such as stainless steel. The clip is suitable for deployment in various body elements of a patient, such as tissue or fascia in body cavities, hollow viscus organs, blood vessels and the like. The clip preferably is formed with a first leg 41 having a first end 31, a second leg 42 having a second end 32, a first arcuate portion 33 configured in the first leg, a second arcuate portion 34 configured in the second leg; and a third arcuate portion 35 configured between the first arcuate portion and the second arcuate portion. The shape formed by the legs and arcuate portions is sinusoidal or "W"-like. The clip is constructed in a manner that provides preferential bending and straightening at the third arcuate portion when the clip is deployed into patient tissue, for example, a vein valve.

The first and second ends 31 and 32 of the clip 30 are each sharpened or otherwise made to form a slanted edge and preferably a sharp point which will pierce, for example, a vein valve and wall. The slanted edges may be formed in various configurations, for example, directed toward or away from each other. In addition, a first arcuate portion 33 is configured a distance "C" from the first end of the clip, extending from the first leg 41. Similarly, a second arcuate portion 34 is configured a distance "C" from the second end, extending from the second leg 42. The distance "C" is sized so that when the legs pierce through a valve leaflet, into a vein wall, the legs penetrate the vessel wall and the first leg passes the second leg, placing the ends in close proximity and closing the clip.

The amplitude "D" of the arcuate portions must be of a sufficient length to ensure that the clip properly pierces the vein leaflets 37, 38 and secures the clip 30 to the vein wall 45. Similarly, the amplitude "D" is configured to ensure the legs 41, 42 fold with an appropriate level of force. In addition, the distance "E" from the first end 31 and along the first leg 41 to the first arcuate portion 33 and even with (along the same plane as) the midpoint 44 of the middle arcuate portion 35 must be of a sufficient length to allow the first leg to pierce both the valve leaflet and the vein wall. The distance "E" between the first and second arcuate portions is preferably of a sufficient length to permit the clip to span the valve leaflets, while allowing the first and second ends of the clip to cross when the clip is bent.

Preferred and exemplary dimensions of a clip 30 for use in a vein valve include a tip-to-tip dimension (A) of about 2.3 millimeters (mm). The distance (C) from each of the ends 31, 32 of the legs 41, 42 to a plane even with the midpoint of the first and second arcuate sections 33, 34 is about 2.2 mm. The radius of curvature of each of the first and second arcuate sections is about 0.01 inches (0.25 mm). The middle arcuate section 35 is configured between the first and second arcuate sections, exhibiting a sinusoidal shape, with the legs extending to form a "W"-shape. The radius of curvature of the middle arcuate section is about 0.25 mm. Thus, the midpoints of the first and second arcuate sections are configured at a distance (B) of about 1.9 mm. The amplitude (D) of the middle arcuate section is about 0.8 mm, and the distance (E) from the midpoint of the middle arcuate section to a plane even with the first and second ends of the clip is about 1.4 mm. The body of the clip is made of a wire or similar bendable material having a thickness or diameter in the range of about 0.002 to 0.006 inches (0.05 to 0.15 mm). The preferred clip for use in a vein valve is formed from 0.004 inch #420 stainless steel round wire flattened to about 0.0025 by 0.005 inches.

The dimensions of the clip disclosed herein are relative to the dimensions of the delivery device and the vein valve to be repaired. Such dimensions may change with different applications of the clip and delivery device and are not intended to limit the invention to a single configuration.

As depicted in FIG. 4, the distal or working end 51 of the delivery device or catheter 50 of the present invention is configured for deploying the clip appliance 30 in a body lumen or cavity, such as a viscus or blood vessel, e.g., proximate a vein valve. The working end includes a slotted housing 55, comprising an elongate tubular member, for example, a stainless steel cannula. The slotted housing is configured for containing the valve clip 30, or a bundle of clips, and the deployment mechanism, and is formed from a biocompatible material, such as stainless steel or a suitably sturdy polymer.

The working end of the delivery device 50 further includes a distal tapered tip 60. The proximal end 62 of the tapered tip is secured to the distal end 56 of the slotted housing 55. The slotted housing includes a clip eject slot 58 which is aligned with a clip guide recess 65 configured in the tapered tip. The clip appliance 30 is retained within the tapered tip recess and is released through the eject slot during deployment of the clip. An inflatable member or actuator balloon 130 and actuator arm 100 deploy a clip around an anvil 95 positioned adjacent the eject slot of the housing and configured at the distal end of an anvil retainer arm 90. Inflation of the actuator balloon moves the actuator arm and clip radially within the slotted housing toward the anvil.

The proximal end 102 of the actuator arm 100 is secured within a slot 73 in a plug 70 fixed within the proximal end of the slotted housing 57 (FIG. 4A). The anvil retainer arm 90 is disposed over and secured to a slide tube 80 which is moved longitudinally by means of a slide wire 75 slidably disposed within a lumen in the plug. An anvil guiding tube 85, having a proximal end 87 secured within the plug, provides fixed support to the slide tube and retainer arm.

As also shown in FIG. 4B, the retainer arm 90 is slidably disposed within the slotted housing 55 and is disposed on and secured to an anvil slide tube 80. The slide wire 75 is secured to the anvil slide tube, which is slidably disposed over the anvil guiding tube 85. The inflatable member or actuator balloon 130 is positioned, in its deflated condition, on the radially opposite side of the slotted housing from the anvil retainer arm. A floating tip retainer 110 is secured to the distal end 101 of the actuator arm 100, and is disposed between the balloon and the distal end of the retainer arm. A floating actuator tip 120 is slidably disposed on the distal end of the actuator arm and within the floating tip retainer. The floating tip is configured for engaging the clip 30.

Referring to FIG. 5, the distal end 51 of the delivery device 50 may be turned, twisted and torqued from its proximal end 52. The tapered tip 60 comprises the furthermost distal end of the delivery device. The proximal end the tapered tip is notched, threaded or otherwise configured so as to engage the distal end of the slotted housing 55. The proximal end 57 of the slotted housing is connected to the distal end of a flexible, torqueable elongate tubular member or catheter 145, having one or more lumens for a guidewire, the slide wire 75 or the like. The elongate tubular member is configured of a material or materials sufficiently torqueable, yet flexible, for traversing the selected anatomy of a human patient and is comprised of various materials which are biocompatible with the human anatomy. Such materials include polyether block amide, and other suitable flexible polymers. Such materials may be injected or otherwise made with radiopaque material for visualization under fluoroscopy. In addition, radiopaque markers may be embedded or otherwise secured to the catheter for observation under x-rays for fluoroscopy. Similarly, bubbles can be molded into the catheter for ultrasound visualization.

The proximal end 52 of the delivery device 50 includes a handle 140 for ease of use by the surgeon. The distal end of the handle is connected to the proximal end of the flexible elongate tubular member 145. The handle is preferably configured with an inflation or actuation port 142 and guidewire port 143 comprised of, for example, luer fittings. The guidewire port may also be used for other suitable purposes, such as needle or optical fiber introduction and contrast or flush injection.

In addition, the handle 140 contains a slide mechanism 144 used to release the clip appliance 30. The slide wire 75 resides in a lumen of the flexible portion of the catheter 145, extending through the patient's vasculature and is manipulatable by the user or physician via the slide mechanism. The slide wire is elongate and sufficiently flexible to traverse the patient's anatomy, in particular the vein and valves to be repaired. The proximal end of the slide wire is secured to the slide mechanism, so as to move the slide wire and anvil retainer arm 90 in a longitudinal direction to position the anvil 95 and cover tab 93 away from the eject slot 58, allowing the clip to leave the delivery device (FIG. 4).

For ease of traversing the vein, the delivery device 50 may be configured with an outer sheath (not shown). Such an outer sheath is configured to cover the distal end 51 of the delivery device containing the clip appliance 30 and is coaxial and separately retractable from the slotted housing 55. The distal end 51 of the delivery device is configured to deploy a single or a plurality of clips, and the proximal end 52 is similarly configured.

As also shown in FIG. 6, the slotted housing 55 is made of a generally cylindrical elongate tube configured from stainless steel (hypotube), titanium, plastic or other biocompatible material having suitable structural integrity. The slotted housing has an internal diameter in the range of about one to ten millimeters and with the preferred diameter being two millimeters for use in a vein. The housing is of a suitable length to contain the actuator mechanism, for example, from two to ten centimeters and preferably approximately five centimeters. The clip eject slot 58 is positioned approximately two millimeters from the distal end 56 of the slotted housing, is approximately 0.25 millimeters wide and is approximately two millimeters in circumference. The slotted housing has a through lumen from the distal end to the proximal end 57, having a wall 59 of suitable thickness to maintain its integrity during clip deployment.

As shown in further detail in FIGS. 7 and 7A, the distal end 61 of the tapered tip 60 is preferably arcuate shaped and resembles a cone. A smoothened configuration allows for easier and atraumatic navigation through the vein, particularly through the vein valves. The conical tip is preferably made of stainless steel; however, the distal tip may be made of any suitable biocompatible material, such as titanium.

The proximal end 62 of the distal tip 60 forms a shoulder 63 which is configured for engaging the distal end 56 of the slotted housing 55, and has a diameter in the range of about one to ten millimeters and about two millimeters for use in a vein. A clip guide slot or recess 65 is configured proximate the proximal end of the shoulder for positioning a clip 30 adjacent the clip eject slot 58. The clip guide recess is elongate and generally tubular in shape having a hollowed-out portion for retaining the clip in position. A transverse retaining slot 67 is configured distal of the clip recess and on the outer surface of the shoulder for slidably retaining the anvil 95 and the cover tab 93 of the anvil retainer arm 90. The tapered tip 60 is further configured with a guidewire lumen 64, extending from and through the proximal end to the distal end 61 of the tapered tip. The tapered tip guidewire lumen is aligned with a through lumen 89 in the guiding tube 85 and is further in communication with a lumen in the flexible portion 145 and handle 140 of the delivery catheter 50. These lumens may also be used for perfusion of a flushing or contrast fluid through the catheter and working end of the delivery device.

Referring to FIG. 8, the slotted housing proximal plug 70 is a generally solid cylindrical member having certain lumens and cutouts therein, preferably made of stainless steel or similar sturdy material. The plug is disposed proximate the proximal end 57 of the slotted housing 55 (FIG. 4), and is secured in place by suitable means, such as bonding or press fit. As further shown in FIG. 8A, a round lumen 71 is formed proximate the center of the plug, in which the slide wire 75 is movably disposed. A round lumen 72 also is provided for fixably retaining the proximal end of anvil guiding tube 85. Similarly, a transverse rectangular slot 73 is formed in the distal end of the plug for securing the proximal end of the actuator arm 100. Further, a longitudinal arcuate slot 74 is formed on the wall opposite the guiding tube lumen and adjacent the retainer arm slot for retaining the balloon stem 135 (FIG. 4A). The guiding tube lumen, slide wire lumen and balloon arcuate slot each extend from and through the proximal end to and through the distal end of the plug.

The distal end 76 of the slide wire 75 is secured to an anvil slide tube 80 near the slide tube's proximal end (FIG. 4). The slide wire is secured on the opposite side of the slide tube from where the retaining arm 90 is secured and distal to the slotted housing plug 70. As noted, the anvil slide tube is slidably disposed on the anvil guiding tube 85. As shown in FIGS. 9 and 9A, the slide tube is circular in cross section at its proximal end 82 and is generally tubular in configuration. The distal end 81 of the slide tube is tapered so as to form a truncated point. The taper at the distal end of the slide tube forms an angle 83 of about five degrees.

As shown in FIGS. 10 and 10A, the guiding tube 85 is formed from a generally cylindrical tube of metal, e.g., stainless steel, or may be otherwise formed from a sturdy plastic or similar biocompatible material. The guiding tube includes a round longitudinal guidewire lumen 89, extending from the distal end 86 to the proximal end 87 of the guiding tube. The guiding tube proximal end is secured within a tubular lumen 72 of the slotted housing plug 70 (FIG. 8A). The distal end of the guiding tube is tapered at about a five degree angle 88 to form a truncated point. The guiding tube point is aligned with and extends proximate, but proximal, the clip eject slot 58 of the slotted housing 55. When the anvil slide tube 80 is in its most distal position, the truncated point at the distal end 81 of the slide tube is preferably disposed slightly distal of the guiding tube truncated point, and likewise terminates proximal of the clip eject slot (FIG. 4).

Referring also to FIGS. 11, 11A and 11B, the anvil retainer arm 90 is arcuate in shape, being made from a portion of a stainless steel hypotube approximately 0.1 inches (2.5 mm) in diameter. The anvil retainer arm is secured at its proximal end 92 to the anvil slide tube 80, so that the retainer arm is disposed over the slide tube truncated point 81 (FIG. 4). Consequently, the anvil retainer arm does not contact the anvil guiding tube 85. Instead, the guiding tube and slide tube provide support for the retainer arm. As the slide wire 75 is moved in a longitudinal direction (distal to proximal), the slide tube and anvil retainer arm are moved in a corresponding manner over the guiding tube.

The distal end 91 of the anvil retainer arm 90 tapers and steps to first form a tab 93 configured for covering the clip eject slot 58 in the slotted housing 55. The distal end of the anvil retainer arm (distal the slot cover tab) is further formed with an anvil 95. The anvil is an elongate and rectangular shaped tab configured to be retained within the anvil retaining slot 67 of the catheter distal tip 60. The anvil is of a sturdy material, for example, stainless steel, and sufficiently thick so as tolerate bending of a clip appliance 30 around the anvil during clip deployment. The anvil is not as wide as the eject slot so that the legs of the clip may protrude through the eject slot when the clip is formed against the anvil.

Since retainer arm 90 and, therefore, the anvil 95 are fixedly connected to the anvil slide tube 80, the anvil may be moved proximally and distally as a result of proximal and distal movement of the slide wire 75. When the anvil is in its most distal position, it is retained within the slot 67 in the tapered tip 60 (FIG. 4). When the anvil is in an intermediate position, then the anvil is positioned directly over the clip guide recess 65 of the tapered tip and just below the clip eject slot 58 of the slotted housing 55. When the anvil is at its most proximal position, then the anvil and distal end 91 of the anvil retainer arm are positioned proximal the clip guide recess and clip eject slot, allowing a clip appliance 30 to move out of the delivery device 50.

As shown in FIG. 12, actuator arm 100 is elongate and rectangular in cross-section, being formed from a sturdy material, such as stainless steel. The distal portion 101 of the actuator arm is tapered and configured with a rectangular tab 105, which is slidably disposed within the clip guide recess 65 of the catheter distal tip 60 (FIG. 4). At approximately one-half of the distance between the proximal and distal ends, the actuator arm is bent at approximately a ten degree (10°) angle. The bend 106 configured so that the tab at the distal end of the actuator arm rests proximate the inside wall 59 of the slotted housing 55 and opposite the clip eject slot 58. The bend also provides a space between the actuator arm and the slotted housing wall for the deflated balloon 130. The proximal end 102 of the actuator arm 100 is secured within the transverse slot 73 of the plug 70, and does not move as the slide wire 75 is moved proximally or distally (FIG. 4A). Movement or biasing of the actuator arm in a radial direction toward the eject slot will cause the distal end of the actuator arm to engage a clip 30 and force the clip against the cover tab 93, the anvil 95 or through the eject slot, depending on the longitudinal position of the retainer arm 90.

As shown in FIG. 13, a floating tip retainer 110 is secured by weld, glue or other similar means to the distal portion 101 of the actuator arm 100 and proximal the actuator arm distal tab 105. The floating tip retainer is generally rectangular on its sides and rectangular in cross section, forming an open ended box-like enclosure. The tip retainer tapers longitudinally to snugly fit over the actuator arm, but has a height greater than the thickness of the actuator arm. The actuator arm is secured within the retainer so as to provide a retaining lumen 112 on the side of the arm toward the eject slot 58.

An elongate floating actuator tip 120 is slidably disposed within the floating tip retainer 110 at the distal portion 101 of the actuator arm 100. As shown in more detail in FIG. 14, the floating actuator tip is rectangular in cross section having dimensions of about 0.01 inches (0.25 mm) by 0.005 inches (0.13 mm). The actuator tip has an approximate length of ten millimeters, sized to remain slidably disposed within the lumen 112 of the tip retainer as the actuator arm moves in a radial or transverse direction within the slotted housing 55. The proximal end 122 of the floating actuator tip is slidably disposed within the floating tip retainer to provide sufficient support for the floating tip such that a biasing force applied to the actuator arm will be transferred to the distal end 121 of the floating actuator tip.

At the distal end 121 of the floating actuator tip 120, a flange 125 is provided at approximately a ninety degree (90°) angle away from the actuator arm 100 and is disposed toward the inner portion and eject slot 58 of the slotted housing 55. The floating tip flange is approximately one millimeter wide having an arcuate edge 127, configured to span the distance between the first arcuate section 33 and the second arcuate section 34 of the valve clip 30. Preferably, the arcuate edge of the floating tip flange is concave; however, in certain applications, the flange may be convex or otherwise suitably shaped, so as to specifically direct the force from the actuator arm.

The floating actuator tip flange 125 is configured to engage one clip appliance 30 at a time when the actuator arm 100 moves in a radial direction toward the eject slot 58 of the slotted housing 55. As force is applied to the actuator arm, the force will be propagated to the actuator tip and to the clip, thereby pushing and flattening the middle arcuate portion 35 of the clip against the anvil. The arcuate flange is specifically configured to engage the clip so as to maximize penetration of the first and second legs 31, 32 of the clip into the patient viscus or vessel, to enhance straightening of the third arcuate portion, and to maximize crossing of the first and second legs prior to releasing the clip through the eject slot.

Figure 15:
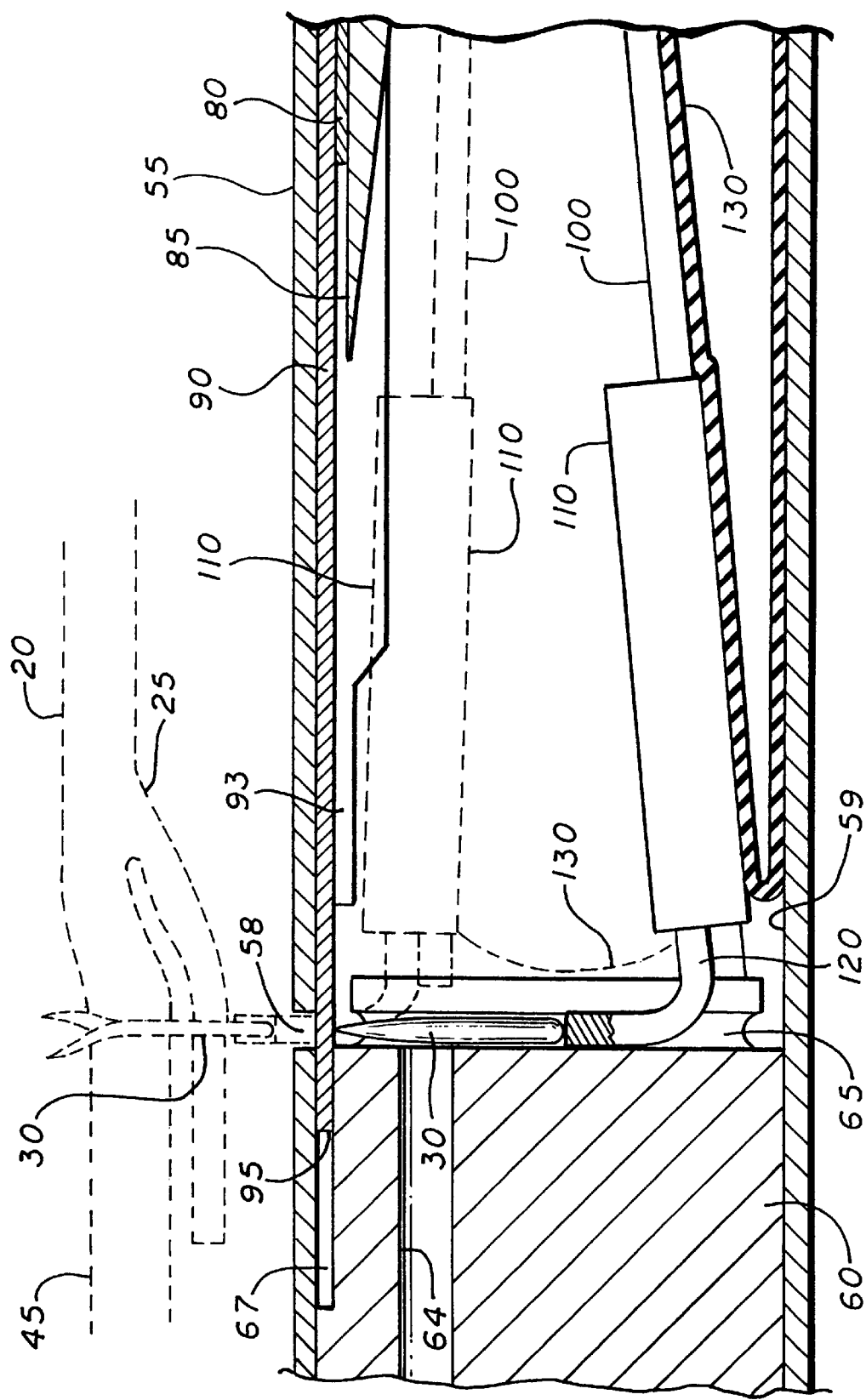
FIG. 15 is a side elevational view of the inflated balloon having moved the actuator arm of the delivery device of FIG. 4 to engage a clip of FIG. 3.

As shown in FIGS. 4 and 15, an inflatable member or actuator balloon 130 is configured within the slotted housing 55, between the housing wall 59 and the actuator arm 100. In its normally deflated position, the balloon resides within the arcuate space formed by the bend 106 of the actuator arm. The balloon extends from proximate and distal the proximal plug 70 to proximate and proximal the distal end 101 of the actuator arm. The distal end 131 of the actuator balloon is positioned just below the floating tip retainer 110 and floating actuator tip 120. The proximal end 132 of the balloon is secured to a balloon leg 135, which resides within the longitudinal arcuate slot 74 of the proximal plug. The balloon leg contains an inflation lumen, which is in fluid communication with the actuation port 142 in the delivery device handle 140 (FIG. 5).

As shown in the hidden view of FIG. 15, when the actuator balloon 130 is fully inflated, the expansion of the balloon causes a force on the actuator arm 100 which moves the actuator arm away from the slotted housing wall 59 and toward the anvil retainer arm 90. Movement of the actuator arm correspondingly moves the floating tip 120 and floating tip retainer 110 to a radial position proximate the clip eject slot 58 in the tapered tip 60. The flange at the distal end of the floating actuator tip moves within the clip guide recess 65 of the catheter tapered tip.

When the anvil slide wire 75 is in its most distal position, the valve clip 30 is prevented by the tab 93 on the anvil retainer arm 90 from exiting the clip eject slot 58. When the anvil actuator wire is moved proximally, such that the anvil 95 is positioned above the clip guide recess 65 and below the clip eject slot 58, pressure on the floating actuator tip 120 will cause the valve clip legs to exit the clip eject slot and to pierce the vein wall. Under such a force, the clip moves within the tapered tip recess until the middle arcuate section 35 of the clip contacts the anvil. Increased pressure (force) from the balloon and actuator arm causes the clip to bend around the anvil and valve commissure (FIG. 2). When the anvil is in the intermediate position, the force of the balloon on the actuator arm and the actuator tip bends the clip through the eject slot in the slotted housing, through the valve leaflets 25 and the vein wall 45 until the middle arcuate section 35 straightens to cross or interlock the first and second legs 41, 42. When the anvil is moved to its most proximal position, the force of the balloon on the actuator arm causes the floating actuator tip to completely eject the clip through the slot in the housing, thereby releasing the clip from the delivery device. The diverting balloon or inflatable member is used to stabilize the position of the clip eject slot of the housing and the clip against the vessel wall while the clip is being released.

The method of the present invention may be specifically adapted to, but is not intended to be limited to, a procedure for minimally invasive valvuloplasty for treatment of chronic venous insufficiency. With reference to FIGS. 16 through 20, the method of intraluminal deployment of a clip in a vein valve is described for use with the clip appliances and delivery devices described heretofore. The method, however, may be adapted for use with any suitable clip appliance for repair of incompetent venous valves, or alternative embodiments of the delivery device, for example, the embodiments disclosed herein.

To start the procedure for vein valve repair, the patient is placed onto a gurney or procedure table (not shown). Optionally, the feet can be positioned to fill the veins of the leg with blood. The ankle of the patient is prepped with antiseptic solution. The leg is tourniqueted with a band proximal to the site of the puncture and the vein is entered with an 18# or similar introducer needle. A cutdown could also be performed rather than using the needle to enter the vein. The tourniquet is then removed.

A guidewire (not shown) is inserted into the vein according to the well known and practiced Seldinger technique and the needle is removed. The wire is advanced to the level of the incompetent valve to be repaired. Alternatively, the delivery device could be passed within the vein after insertion through the skin, without the need to advance the wire to that level. A sheath can be inserted into the vein to provide vascular access. Fluoroscopy, x-ray, ultrasound, angioscopy or a similar imaging technique is then used for specific placement of the catheter and confirmation of position.

If the delivery device is inserted percutaneously at a more distal part of the vein, then the device is advanced to the affected valve. Preferably, the clip guide recess can be observed under the fluoroscope to determine the position and orientation of the valve clip. Further, the delivery catheter may have radio-opaque markers which provide for rotational and depth orientation and alignment within the vessel under fluoroscopic guidance. Alternatively, the delivery device could incorporate a fiberoptic bundle for direct visualization of the valve and catheter position. Such a fiberoptic design would incorporate an irrigation port through which saline or another optically clear solution could be injected to clear blood from in front of the catheter. Alternatively, an independent fiberoptic scope could be inserted from above the valve to allow visualization of the clip placement onto the valve.

Figure 20:
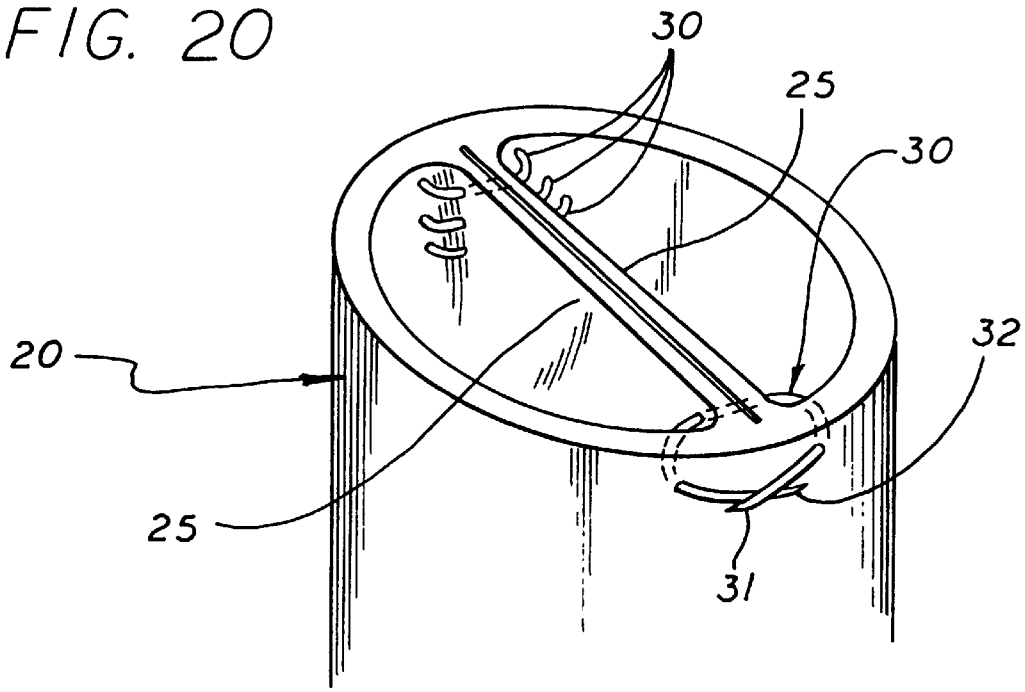
FIG. 20 is a perspective view showing multiple valve clips deployed into a vein valve.

After appropriately placing the device and positioning it at the level of the valve, the delivery device then advances the clip into the valve leaflets at the commissure and through the wall of the vein. Force is applied to the clip to straighten it in such a way as to embed the legs of the clip into the valve and wall. The process is repeated to place more than one clip on a valve. Multiple clips may by placed on each side of the valve (FIG. 20).

Certain embodiments of the delivery device include the capability of simultaneously or sequentially placing a plurality of clips on the valve, e.g., two clips placed one hundred eighty degrees apart on the circumference of the vessel or valve. After placement of the clips, the working end of the delivery device would be moved to a valve located caudal (distal from the heart) for the next repair, and finally would be removed from the vessel with hemostasis accomplished either by local pressure alone or with one or more sutures at the skin insertion site. To best prevent damaging valves that have been "clipped" (repaired), the most proximal valves (closest to the heart) are treated first. For repairing a vein in a leg of a patient, preferably the most proximal incompetent valve would be repaired first, then the catheter is partially withdrawn to the next (distal) incompetent vein valve.

Figure 16:
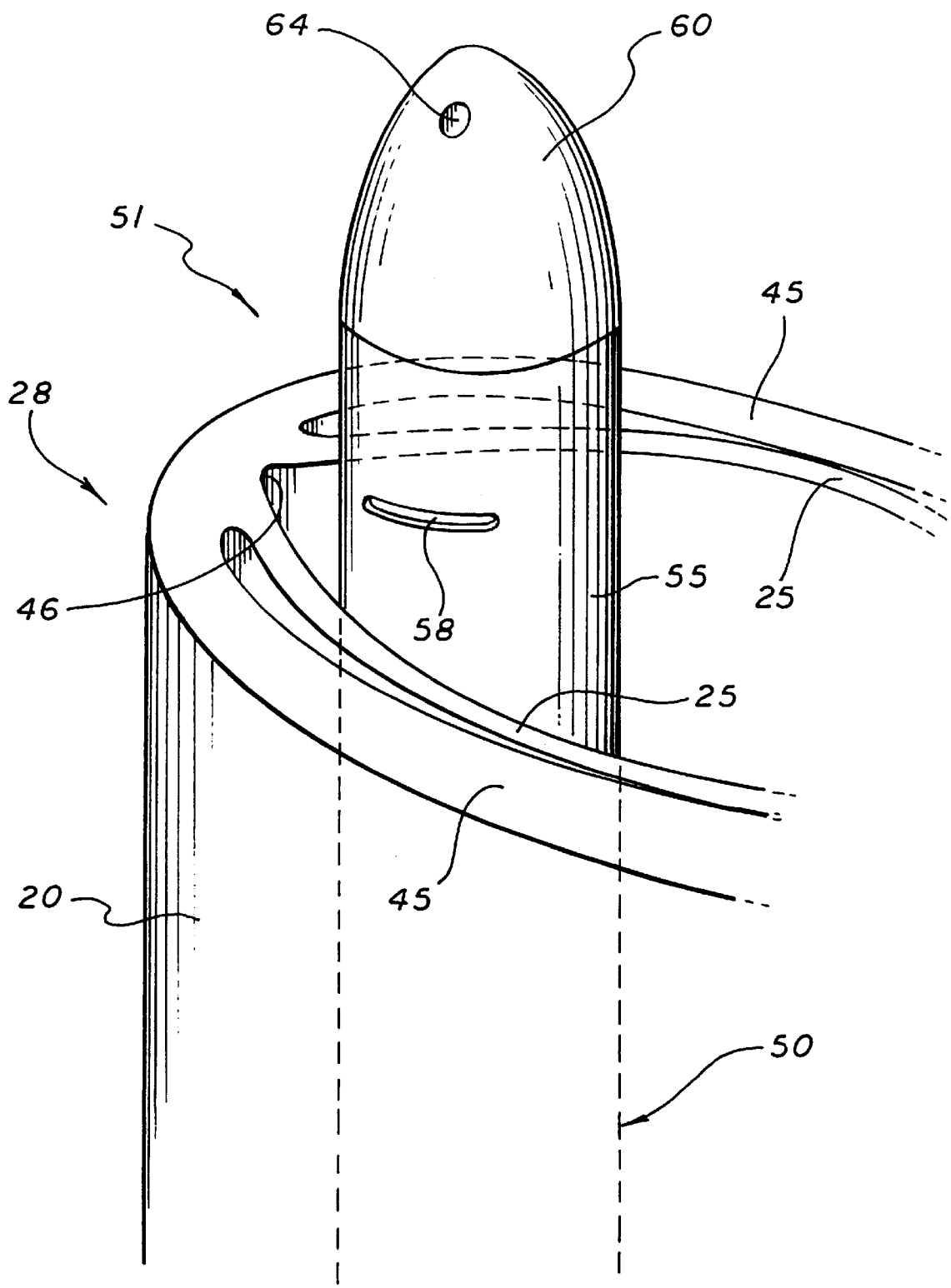
FIG. 16 is a perspective view of the delivery catheter of the present invention positioned proximate a commissure of an incompetent valve.

As shown in FIG. 16, the deployment device or catheter 50 is inserted through the vasculature so as to position the distal tapered tip 60 and slotted housing 55 proximate the incompetent valve 28 which is to be repaired. The approximate position of the working end 51 of the delivery catheter may be aligned with the valve by well known fluoroscopic techniques. Additional radiopaque markers may be embedded within the catheter and slotted housing for proper positioning of the delivery device. Because the slotted housing is of a diameter somewhat smaller than that of the vein 20, the valve leaflets 25 will spread apart upon insertion of the delivery catheter. The diameter of the slotted housing may be selected such that the leaflets will be pressed against the vein wall 45. The clip eject slot 58 should be positioned at a point upon the leaflet where the valve clip is to be deployed, preferably at the valve commissure 46.

Figure 17:
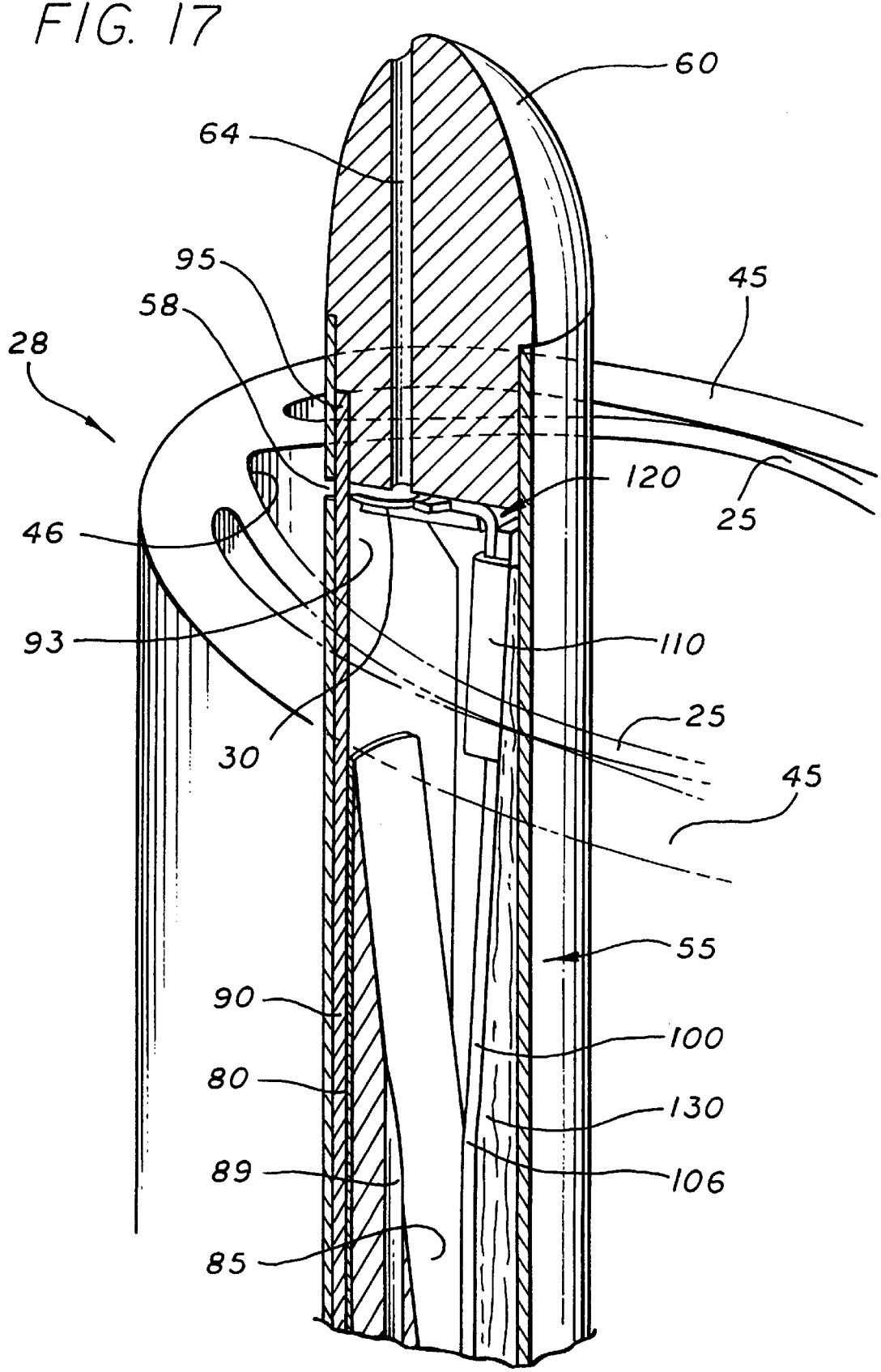
FIG. 17 is a perspective view in cross-section of the delivery catheter of the present invention positioned for deployment of a valve clip.
Figure 22:
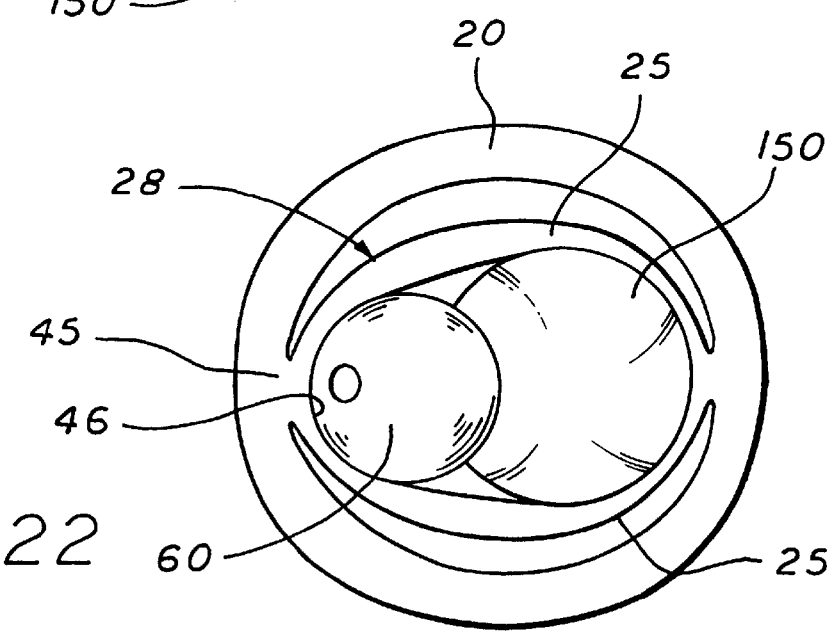
FIG. 22 is a top plan view of the distal section of the delivery device of FIG. 21 showing the biasing balloon in its inflated condition and the clip eject slot positioned adjacent a commissure of an incompetent valve.

As shown in FIG. 17, the working end of the delivery device is further positioned within the vein so as to align the clip eject slot 58 with a location at the valve commissure 46 which will be secured by the valve clip 30. The delivery device is torqued or rotated axially until the eject slot is in the proper alignment. The alignment may be made by fluoroscopic technique or by special alignment, such as use of an LED device. Once the distal tapered tip 60, slotted housing 55 and clip eject slot are properly aligned, the anvil slide wire 75 (FIG. 4) is moved longitudinally to pull the slide tube 80 and anvil retainer arm 90 and anvil 95 to their intermediate position. Also, if a diverting balloon is used, it may be inflated once the eject slot is aligned (FIG. 22).

Figure 18:
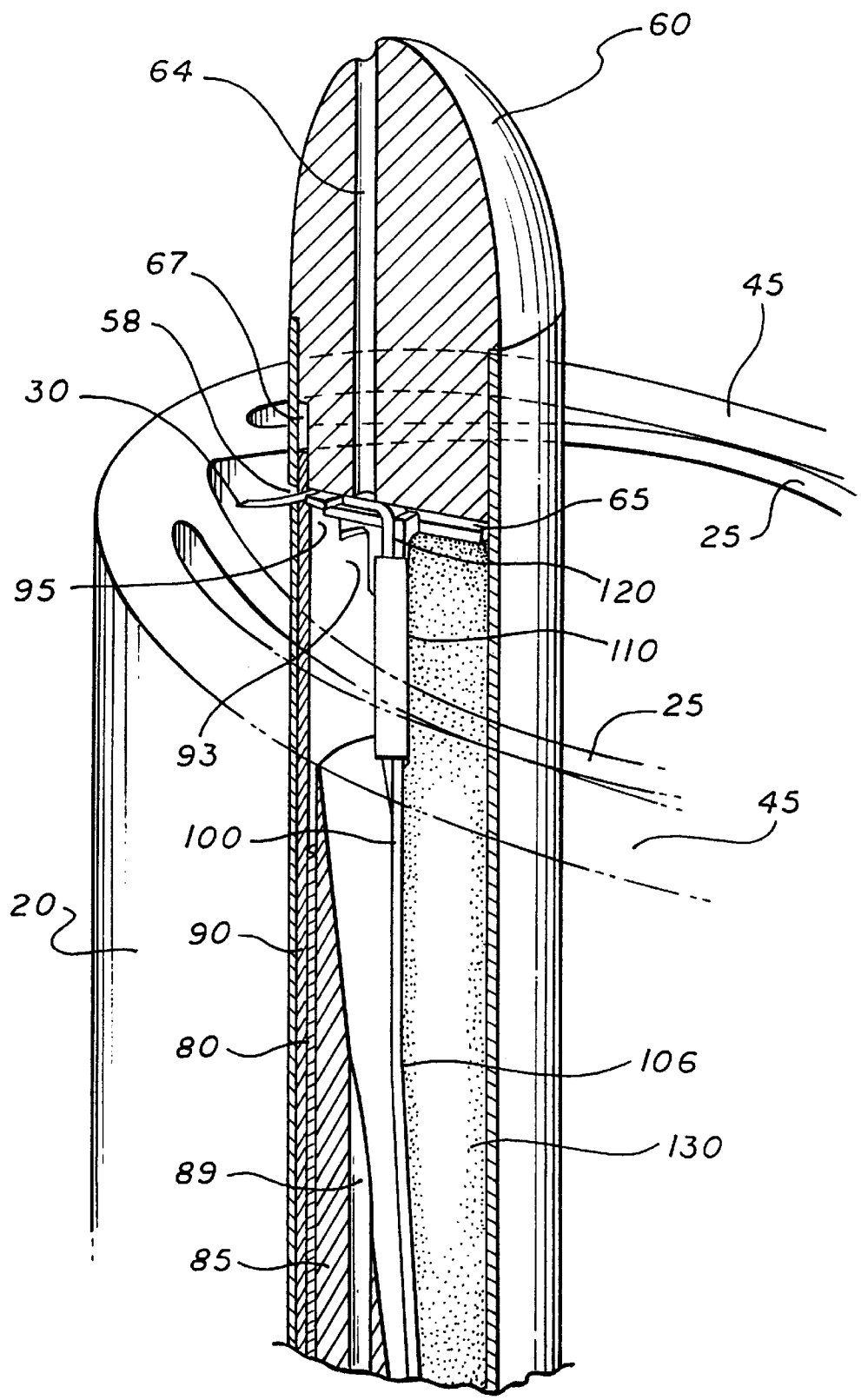
FIG. 18 is a perspective view in cross-section of the delivery catheter of the present invention, wherein the actuator balloon is partially inflated.

Referring to FIG. 18, once the slide wire 75 and slide tube 80 have been moved proximally such that the anvil 95 is positioned between the clip guide slot 65 and housing eject slot 58, the actuator balloon 130 is further inflated so that the legs of the valve clip 30 engage the vein wall 45. The balloon is then fully inflated so as to exert a force on the actuator arm 100 and floating actuator tip 120 to drive the clip firmly against the anvil, thereby pushing the clip legs through the clip eject slot and into the leaflets 25 at the commissure 46 and vein wall. Additional expansion of the balloon and further pressure upon the actuator arm and actuator tip straightens the middle arcuate section of the clip, causing the clip legs to bend around the anvil, through the valve leaflets and through the vein wall. Continued force is applied until the legs of the clip cross and are firmly secured to the vein wall.

Figure 19:
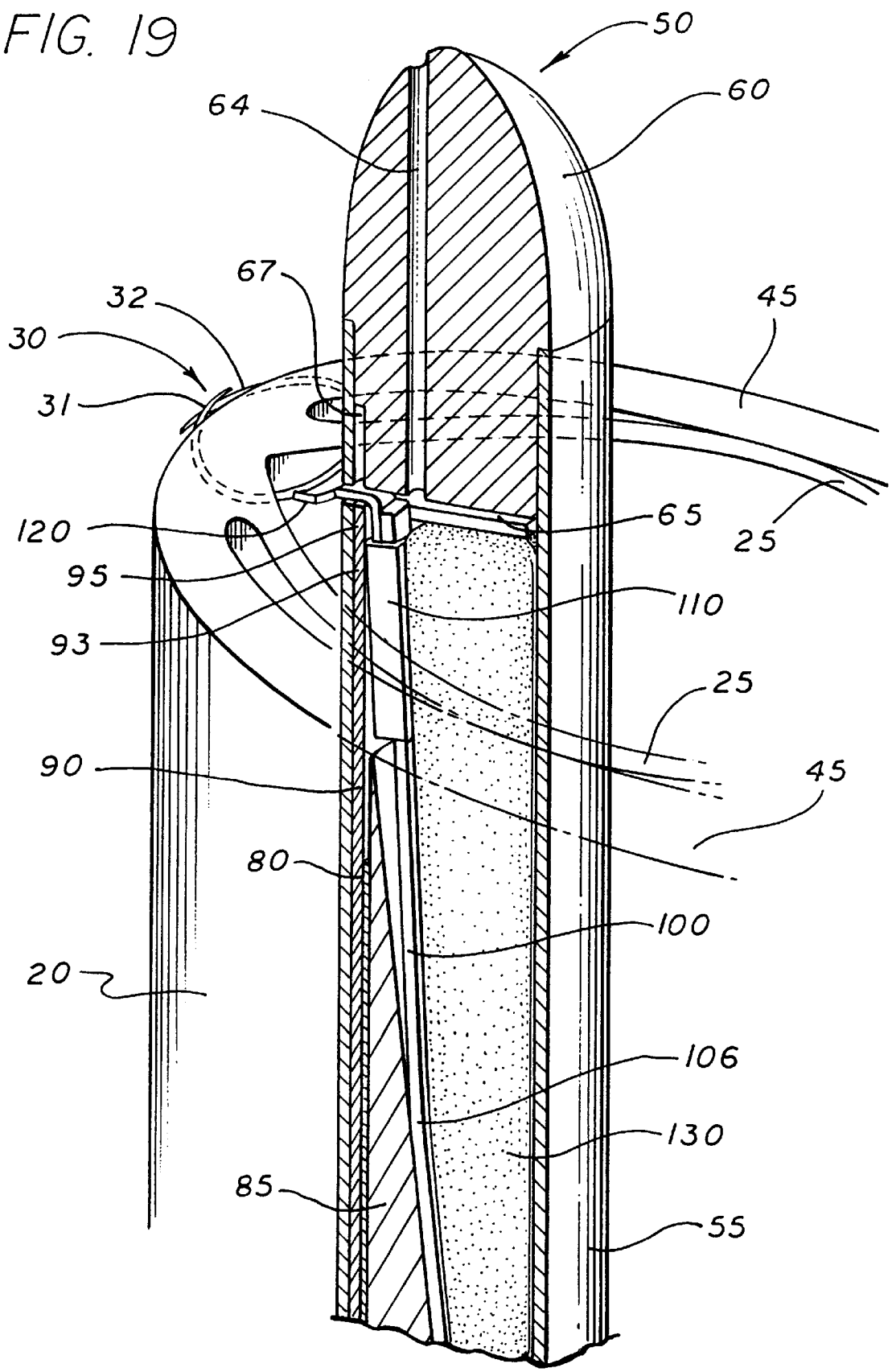
FIG. 19 is a perspective view in cross-section of the delivery catheter of the present invention, wherein the actuator balloon is fully inflated and a valve clip has been deployed into a vein.

As shown in FIG. 19, once the valve clip 30 has been completely bent, the anvil slide wire 75 and slide tube 80 are moved in a proximal direction until the anvil 95 and anvil retainer arm 90 are moved clear of the clip guide recess 65 in the distal tapered tip 60 and the clip eject slot 58 of the slotted housing 55. Once the anvil has moved away from the clip eject slot, the clip is completely released from the delivery device. The actuator arm 100 and floating actuator tip 120 are configured so as to push the clip out of the eject slot once the anvil has been moved away from the clip guide recess.

Once the clip 30 has been released from the delivery device 50, the actuator balloon 130 is deflated and the anvil slide wire 75 is moved distally to move the anvil retainer arm 90 to its distal position, thereby covering the clip eject slot 58. Thereafter, the delivery catheter may be moved to the next valve to be repaired in a multi-clip embodiment, or the delivery catheter may be removed and reloaded with a new clip for deployment into another valve. Alternatively, the deployment catheter may be repositioned at the same valve to the same or opposite commissure or leaflet and a second clip applied. As shown in FIG. 20, once one or more clips have been properly deployed, the valve returns to its competent state.

The present invention includes a method of restoring vein valvular competence using the clip appliance and delivery device as disclosed herein. One embodiment of the restoration method includes tightening certain loose vein valve leaflets contributing to valvular competence. Loose leaflets cause multiple folding of the valve leaflets to occur, preventing a complete seal at the valve. Similarly, loose leaflets may prolapse, causing an incomplete seal at the valve and reflux of blood flow. To tighten the valve leaflets, the delivery device is positioned with clip eject slot proximate a commissure of a vein valve, as described heretofore. A clip appliance is then deployed into the loose vein valve leaflets such that the clip appliance pins the loose leaflets against the inner vein wall, thereby reducing vein valve leaflet looseness. Multiple clips can be deployed through the leaflets and axially across the valve to further improve competency.

Another embodiment of the restoration method includes reducing the circumference of a vein valve which has dilated, thereby contributing to valvular competence. Deployment and bending of a clip appliance at or immediately adjacent to (proximal or distal) a vein valve will cause the vein wall to be pinched together and further improve the restoration of vein valve incompetence. Restoration of valvular competence is accomplished when the vein diameter reduction causes the valve leaflets to be drawn closer together so as to provide more contact surface between the bicuspid valve leaflets. Increasing the contact surface area between leaflets helps prevent prolapse of the leaflets and therefore prevents reflux of blood when venous hypertension or reverse blood flow places sufficient pressure on the valve leaflets to close them forcefully.

Figure 21:
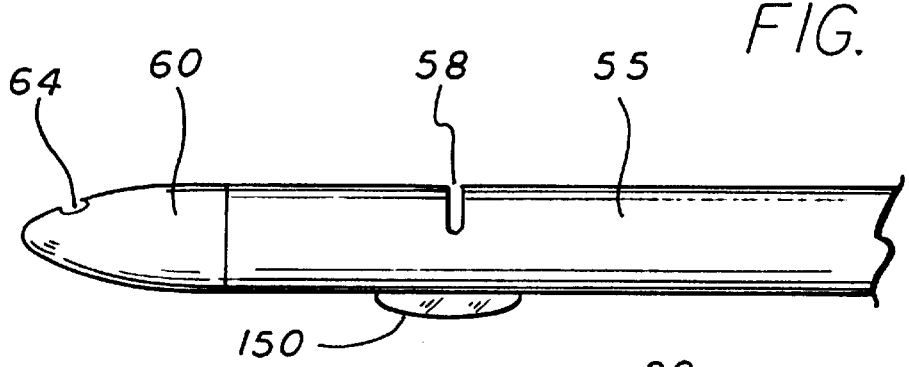
FIG. 21 is a side elevational view of the distal section of an alternative embodiment of the delivery device showing a biasing balloon opposite the clip eject slot.

As shown in FIGS. 21 and 22, an alternative embodiment of the working end a delivery device may be configured such that the slotted housing 55 further includes an external biasing device, such as an inflatable member or diverting balloon 150. The inflatable member is positioned on the side wall of the slotted housing proximal the tapered tip 60 and opposite the clip eject slot 58. When inflated, the diverting balloon is sufficiently large, for example, one to three times the outer diameter of the slotted housing, so as to push the slotted housing and clip eject slot against the commissure 46 of the incompetent vein valve 28.

Such a configuration allows the valve clip to be positioned close to the vein wall 45 and leaflets 25 during deployment. Likewise, the slotted housing is stabilized near the commissure 46 of the vein valve during clip deployment. Alternatively, the valve clip may be deployed prior to full inflation of the diverting balloon so that the legs of the clip pierce the leaflets some distance away from the commissure. Early deployment of the clip provides additional tightening of the valve leaflets once the diverting balloon is fully inflated and the clip is fully deployed and bent into the vein wall.

An inflation lumen for the diverting balloon 150 is further configured within the slotted housing, catheter and handle (not shown). A corresponding inflation port is also provided in the handle. Alternatively, the same inflation lumen may be used for the actuator balloon 130, wherein the external diverting balloon inflates prior to the internal actuator balloon. When the same inflation lumen is used, the diverting balloon biases the slotted housing against the vein valve prior to deployment of the clip by the actuator balloon. The biasing balloon is especially beneficial when the diameter of the slotted housing is significantly smaller than the inner diameter of the viscus or vessel being repaired.

As shown in FIG. 23, an alternative embodiment of a clip 155 having a first leg 41 with first end 156 and having a second leg 42 with second end 157 is provided to minimize contact between the legs during deployment. As shown in more detail in FIG. 23A, the first end is configured with a first slanted edge 158 directed ninety degrees (90°) from the plane of the clip (toward the side). Similarly, the second end is configured with a second slanted edge 159 directed perpendicular or about ninety degrees (90°) from the plane of the clip and about one hundred eighty degrees from the direction of the first slanted edge (FIG. 23B).

Applying force to the clip arcuate sections 33, 34, 35 causes the middle portion of the clip 155 to straighten and the legs to bend inwardly, as shown in FIG. 24. Because of the side and opposite directed slanted edges 158, 159 on the leg tips 156, 157, providing a shear plane (ride) perpendicular to the plane of the clip, the first leg 41 will have a tendency to pull out of the plane of the clip and away from the second leg 42. Likewise, the second leg will pull out of the clip plane and away from the first leg. Thus, as shown in FIG. 25, the legs pull away from each other, preventing undesirable contact between the clip legs during deployment. In addition, the ride of the leg tips will cause the legs to anchor the clip so as to provide a positive cleating in a third axis of the vein wall.

The cross-sectional shape of the wire or other material used to manufacture the clip will affect the bending characteristics of the clip during deployment. As shown in FIG. 26, the clip legs 41 may be constructed of a material, such as stainless steel, which is generally elliptical or cylindrical in shape, wherein the tip face or slanted edge 31 forms an ellipse. The shape of the slanted edge will effect the particular result of the bending. As depicted in FIG. 27, the leg 160 of the clip may be rectangular or square in shape, causing the first slanted edge 161 to form a rectangle, rhomboid, square or other parallelogram.

The difference in resistance between the front and back of the slanted edge will cause the leg to bend while piercing the tissue of a vein or other body part. Thus, selecting a particular configuration of the slanted edges of the clip tips provides for preferential bending and straightening of the middle arcuate portion 35 of the clip 30 as the clip pierces a vein valve or other tissue. As shown in FIGS. 2 and 3, the slanted edges may be directed in opposite outward directions. Conversely, both slanted edges may be directed inwardly and facing each other. Further, one slanted edge may be directed outward, while the other slanted edge is directed inward. In addition, the angle of the slanted edge may be varied to increase or decrease the degree of bend of the legs.

Referring to FIG. 28, the leg 162 of a clip may be sharpened and curved inwardly to provide an arcuate slanted edge 163 such that the most distal tip of the arcuate edge forms a sharp point for piercing a vein or other body member. The angle of the arcuate edge will determine how the clip leg traverses from one plane to another as the leg meets resistance within the mass of the vein wall or other tissue. Altering the angle of the arcuate edge will affect the penetration angle of the leg.

As shown in FIG. 29, an alternative embodiment of a clip 165 is formed from a triangular wire to specifically direct the force from the actuator arm and anvil of the delivery device. The triangular wire provides a triangular slanted edge 166 at the tip of the clip leg. The inside of the wire is flat, providing a flat surface 167 at the middle arcuate section 35. The flat surface provides increased contact area with the anvil, as opposed to the round wire configurations. Conversely, the outside edge 168 of the triangular wire is pointed at the first and second arcuate sections 33, 34. Thus, the actuator tip of the delivery device will contact the pointed outside edge of the wire. Alternatively, the outside edge of the triangular wire may be flat, while the inside edge contacting the anvil is pointed.

It should be apparent to those skilled in the art that the various material and slanted edge configurations disclosed herein (FIGS. 26–29) may be used interchangeably with the several clip designs disclosed (FIGS. 3, 23). For reference purposes, the body of the clip, including the arcuate portions, generally lie in or form a first plane. However, the legs and/or arcuate sections of the clip may be formed out-of-plane prior to deployment, so as to purposefully direct the bending of the legs when force is applied to the clip during deployment (FIG. 29). Specifically, deployment of the clip in a vein valve bends the first leg away from and out of the first plane and the second leg bends away from the first plane and away from the first leg. Similarly, the third arcuate portion may be bent such that the first arcuate portion lies at an angle to the first plane and the second arcuate portion lies at an angle to the first plane and in a direction about one hundred-eighty degrees from the first arcuate portion. Accordingly, alterations to the clip eject slot, anvil and actuator tip may be provided to accommodate variations in clip design.

Figure 30:
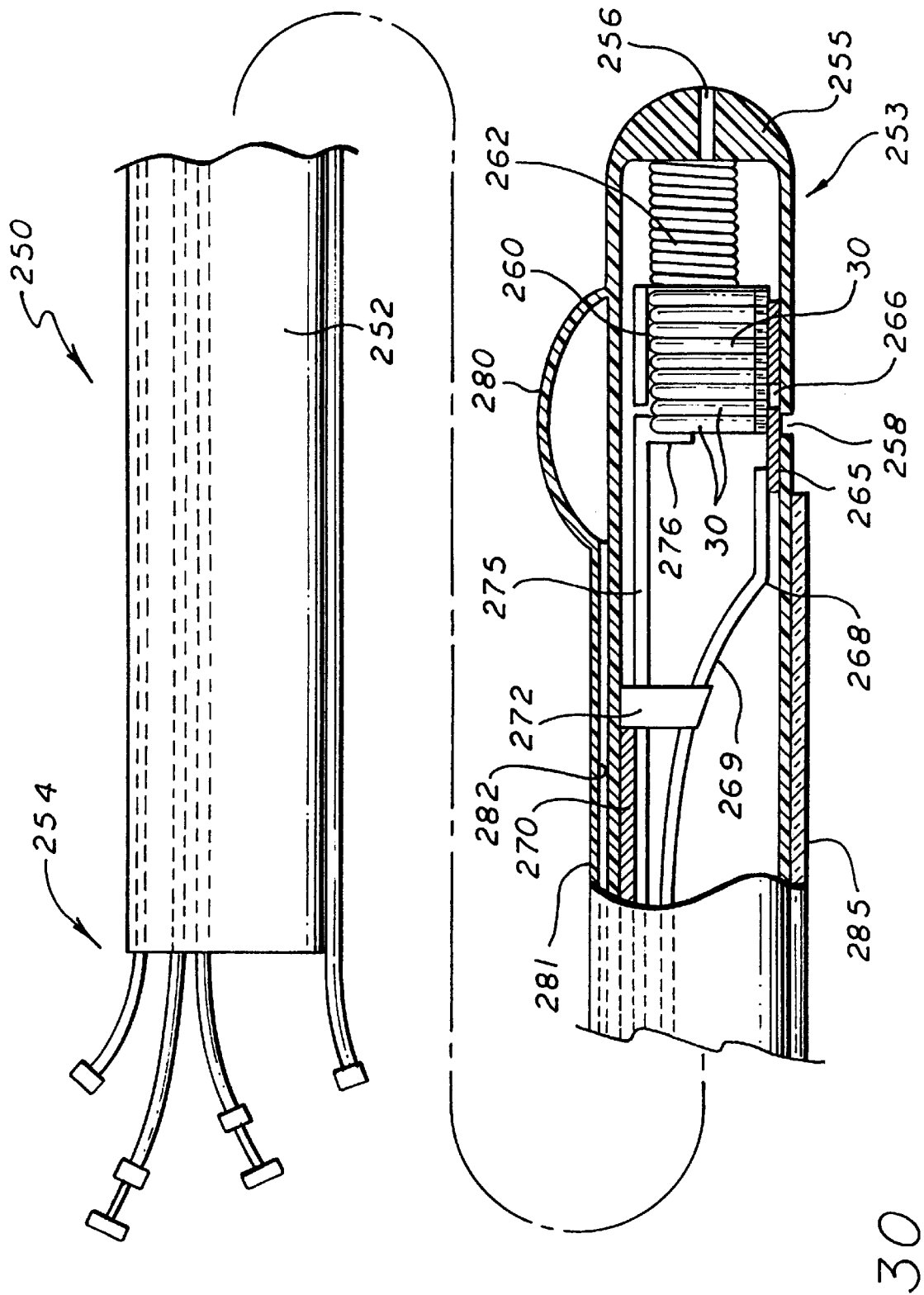
FIG. 30 is a side elevational view in partial cross-section of an alternative embodiment of the delivery device of the present invention comprising a force wedge and an actuator arm.

FIG. 30 shows an alternative embodiment of a delivery device 250 employing an actuator mechanism employing a force wedge for delivering a plurality of clips 30. The delivery device comprises a first elongate tubular member or catheter 252 having a distal end 253 and a proximal end 254. The elongate tubular member is configured with a plurality of lumens or a single lumen housing several catheters, wires and the like. The proximal end of the catheter contains a plurality of ports for fluid injection, balloon inflation, guidewire insertion, etc. The proximal end may also be configured with a handle, as heretofore described.

The distal or working end 253 of the catheter 252 is configured with a tapered tip 255 having a through lumen 256 for a guidewire (not shown). The catheter distal end is further configured with a clip eject slot 258 formed in the catheter wall proximate and proximal the tapered tip. The clips are disposed within a track 260 adjacent the clip eject slot and proximal the tapered tip. A biasing spring 262 is positioned between the tapered tip and the clip track for moving the plurality of clips longitudinally toward the clip eject slot.

The working end of the delivery device 250 further includes an actuation mechanism for deploying the clips 30 through the clip eject slot 258. The clip eject slot is covered by a shutter 265 slidably positioned between the clips in the track 260 and the clip eject slot. The proximal end of the shutter is secured to a slide wire 268, having a distal straight section, a middle arcuate section 269 and a proximal straight section. The distal straight section is secured to the shutter, the while the proximal straight section extends through the catheter main tubular member 252 to the delivery device proximal end 254.

The shutter 265 includes an aperture 266 which may be longitudinally positioned in alignment with the clip eject slot 258. When the shutter is in its most distal position, the eject slot is completely covered by the shutter and the clips cannot move past the shutter. The shutter is further configured with an "E"-shaped anvil within the aperture such that when the shutter is in an intermediate position so that the anvil is aligned with the clip eject slot, a clip may be bent around the anvil. When the a shutter is in its most proximal position, a fully open portion of the aperture is aligned with the clip eject slot so that a clip may be released from the catheter 252.

The middle arcuate section 269 of the slide wire 268 is disposed within a force wedge or carrier 272. The force wedge is trapezoidal in shape, has a though lumen and is secured to a force wire 270 slidably disposed in the catheter 252. Also disposed within the lumen of the force wedge is a clip platen or actuator arm 275, having a proximal end secured within the catheter housing 252. The distal end of the actuator arm comprises an actuator tip 276, configured to engage and push a clip 30 from the clip track 260 through the shutter aperture 266 and through the clip eject slot 258. As the force wire is moved longitudinally in a distal direction, the force wedge moves over the middle arcuate section of the slide wire, moving the actuator arm and tip in a radial direction toward the clip eject slot. The angled sides of the force wedge and the angle of the arcuate section of the slide wire are selected such that force is exerted on the actuator tip and clip as the force wedge moves distally and radially.

The working end of the delivery device 250 is further configured with an external inflatable member or diverting (biasing) balloon 280 on the opposite side (about 180 degrees) from the clip eject slot 258. A balloon leg 281 having an inflation lumen 282 extends from the proximal end of the catheter to the inflatable member. A Luer port or suitable connector for a syringe or a similar inflation means may be configured at the proximal end of the balloon leg.

Adjacent to and secured to the main tubular member 252 of the catheter is an optical fiber 285 for visualizing the clip deployment. A port for connecting the optical fiber to a camera or other visualization mechanism is secured to the proximal end of the optical fiber at the proximal end 254 of the delivery device. The distal end of the optical fiber is positioned proximate and proximal the clip eject slot 258. The lumen 256 in the tapered tip 255 may be used for supplying a flushing fluid when the optical scope is in use.

As shown in FIG. 31, an alternative embodiment of a delivery device 170 comprises a catheter body 172 having a distal end 173 and a proximal portion 174 extending to a handle as heretofore described. A clip eject slot 175 is configured proximal the distal end of the catheter. The clip eject slot is the termination of an arcuate eject lumen 176. The eject lumen is configured generally radially within the catheter. The eject lumen extends from the clip eject slot toward the distal end of the catheter and at an angle of about one hundred thirty-five degrees (135°). The eject lumen traverses from the clip eject slot at the outer surface of the catheter to the opposite radial portion of the catheter and is in communication with a longitudinal force wire lumen 177.

In addition, a longitudinal through lumen 178 is configured within the central portion of the catheter 172 for guidewire access, contrast or flush ejection or similar purpose. A retainer arm 180 having a distal portion configured as an anvil 182 is slidably disposed within a lumen or slot adjacent the clip eject slot 175. The proximal end of the retainer arm is manipulatable from the delivery device proximal end. As heretofore described, the catheter may be configured with an external diverting or biasing balloon (FIGS. 21–22).

A force wire 185 having a distal end 186 and proximal portion 187 is slidably disposed within the force wire lumen 177. The force wire lumen extends from just proximal the catheter distal end 173, through the catheter 172 and to the most proximal end of the delivery device 170. The force wire may be manipulated by the user or physician at the wire's proximal end. The distal portion of the force wire is formed into a hook-like shape, wherein the distal end 186 of the wire resides within the eject lumen 176.

A clip 30, or plurality of clips, is disposed proximate the clip eject slot 175 (proximal or distal), wherein a clip may be positioned within the eject lumen 176 adjacent the distal end 186 of the force wire. When the force wire 185 is pulled in a proximal direction, the distal end 186 of the force wire is moved proximally and through the eject lumen toward the clip eject slot. As a tension force is applied to the proximal end 187 of the force wire, the force is propagated to the distal end of the force wire and to the clip. When the retainer arm 180 has been moved into a proximal position, wherein the anvil 182 is positioned over the clip eject slot 175, the clip is deployed and formed around the anvil. Thus, the clip may be deployed into a viscus or vessel as heretofore described.

As shown in FIG. 32, an alternative embodiment of a delivery device 190 includes a catheter 192 having a distal end 193 and a proximal portion 194 extending to a handle as heretofore described. A clip eject slot 195 is configured very proximate the distal end of the catheter. The clip eject slot is the termination of a force wire lumen 196 which extends from the clip eject slot to the proximal end of the catheter. The distal portion 197 of the force wire lumen is arcuate shaped, extending proximally and radially from the clip eject slot. A force wire 185 is disposed within the force wire lumen. The distal end 186 of the force wire is slidably disposed in a position proximate the distal portion of the force wire lumen and is configured to push a clip 30 through the clip eject slot.

In addition, a through lumen 199 is configured within the catheter 192 for guidewire access, contrast or flush ejection or similar purpose. A retainer arm 180 is slidably disposed within the catheter having a distal portion configured as an anvil 182 is slidably disposed within a lumen or slot adjacent the clip eject slot 195. The proximal end of the retainer arm is manipulatable from the delivery device proximal end. As heretofore described, the catheter may be configured with an external diverting or biasing balloon (FIGS. 21–22).

A clip 30, or plurality of clips, is positioned proximate the clip eject slot 195 (proximal or distal), wherein a clip may be positioned within the force wire lumen 196 adjacent the distal end 186 of the force wire. As a compression force is applied to the proximal portion 187 of the force wire 185, the force is propagated to the distal end of the force wire and to the clip. As the force wire is pushed in a distal direction through the force wire lumen, the distal end of the force wire engages the clip, pushing the clip through the clip eject slot and around the anvil, bending and deploying the clip as heretofore described.

Figure 33:
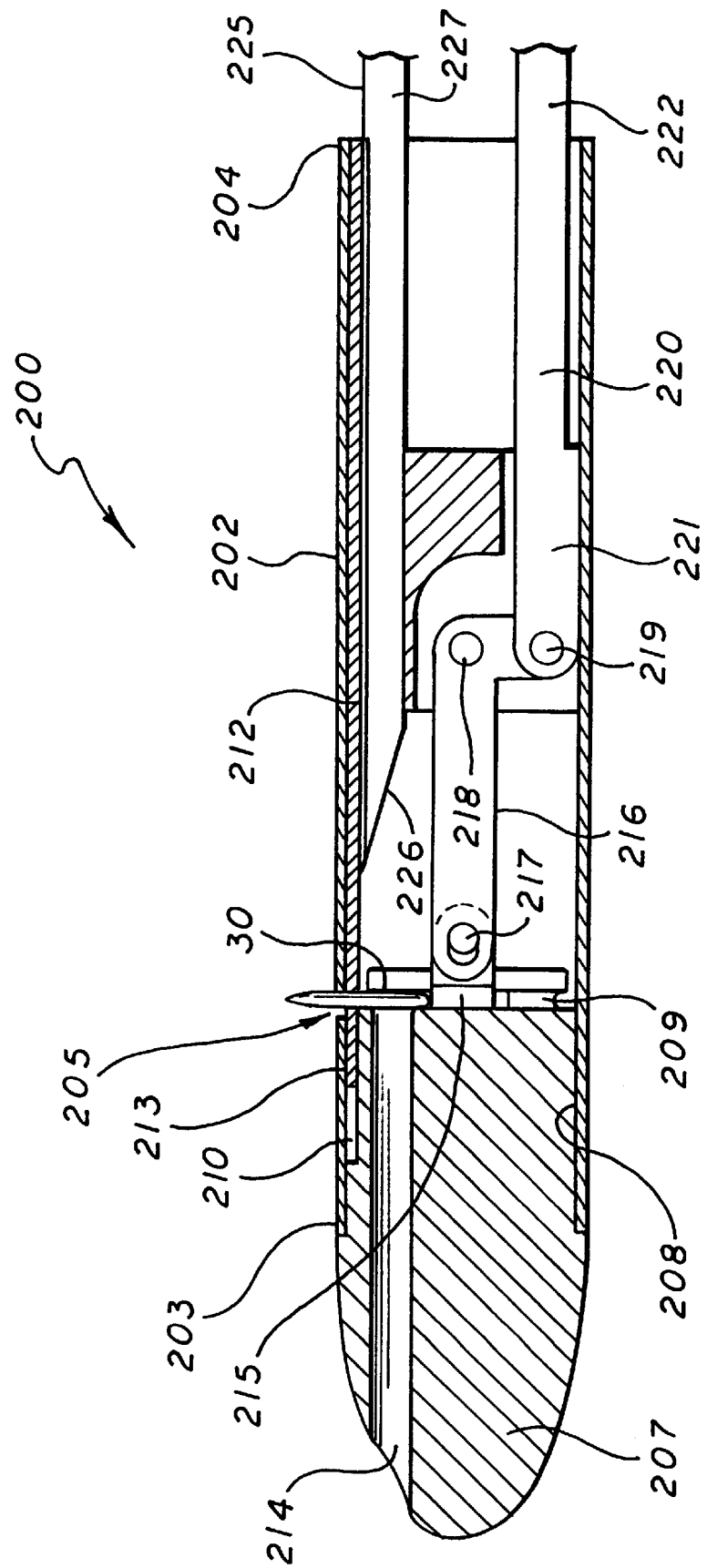
FIG. 33 is a side elevational view in cross-section of an alternative embodiment of the delivery device of the present invention comprising a force arm and pivots.

As shown in FIG. 33, an alternate embodiment of a delivery device 200 having a force arm and force actuator is provided for delivering a clip 30, or plurality of clips. The proximal end of the delivery device includes a catheter, handle and fittings as heretofore described. The distal end of the delivery device comprises a slotted housing 202 having a distal end 203 and a proximal end 204. Configured proximal the distal end of the slotted housing is an eject slot 205 for releasing the clip.

Secured to the slotted housing 202 is a tapered tip 207 having a shoulder 208 which fits within the distal end of the slotted housing. The proximal end of the distal tip is configured with a recess 209 for retaining a clip and guiding it toward the eject slot 205. The tapered tip is further configured with an anvil slot 210 which retains the distal end of a retainer arm 212 forming an anvil 213. In addition, a through lumen 214 is configured within the tapered tip for guidewire access, contrast or flush ejection or similar purpose. As heretofore described, the catheter may be configured with an external diverting or biasing balloon (FIGS. 21-22).

An actuator tip 215 resides within the clip recess 209 of the tapered tip 207 for radially moving a clip 30 through the clip recess to the clip eject slot 205 and around the anvil 213. The sliding actuator tip is slidably disposed within a recess 217 formed in the distal end of a force arm 216. The proximal portion of the force arm is secured to a grounded pivot 218 fixed within the slotted housing 202. The proximal portion of the force arm is L-shaped, wherein the proximal end of the force arm is further secured to a sliding pivot 219.

A force actuator 220 is disposed within the slotted housing 202 and is configured with a distal end 221 secured to the sliding pivot 219. The proximal end 222 of the force actuator extends beyond the proximal end 204 of the slotted housing, through the catheter and is manipulated by the user or physician. By moving the force actuator longitudinally in a distal direction, the force arm 216 pivots around the grounded pivot and sliding pivot, such that the distal end 217 of the force arm moves radially, causing the sliding actuator tip 215 to move radially within the clip recess 209 toward the clip eject slot 205. Similarly, moving the force actuator in a proximal direction moves the actuator tip away from the clip eject slot.

Lastly, a slide wire 225 is disposed within the slotted housing 202. The distal end 226 of the slide wire is secured to the retainer arm 212. The proximal portion 227 of the slide wire extends beyond the proximal end 204 of the slotted housing, through the catheter and may be manipulated by the user or physician. As the slide wire is moved longitudinally in a proximal or distal direction, the retainer arm and anvil 213 correspondingly move in the proximal or distal direction. The anvil is moved to an intermediate position for bending the clip (FIG. 33) and moved to its most proximal position for releasing the clip from the delivery device.

Other potential applications of these devices are for affixing grafts within arterial blood vessels, for accomplishing grafting of vessels and for affixing other hollow structures such as ureters, fallopian tubes, intestines and the like. While several particular forms of the invention have been illustrated and described, it will be apparent that various modifications can be made without departing from the spirit and scope of the invention. For example, references to materials of construction and specific dimensions are not intended to be limiting in any manner and other materials and dimensions could be substituted and remain within the spirit and scope of the invention. Accordingly, it is not intended that the invention be limited, except as by the appended claims.

What is claimed is:

1. A catheter for deploying a clip appliance, the catheter comprising:

a cylindrical housing having a distal end, a proximal end and a side wall, said cylindrical housing having a slot formed proximate the distal end, wherein the slot is configured to provide deployment of a clip through the side wall of the cylindrical housing; and means for deploying a clip through the slot in the side wall of said housing, the means comprising an actuator and an anvil movable independently of the clip and reusable with a plurality of clips, the anvil being controllable to be positioned at the slot to shape each clip prior to deployment of the clip, and to be moved away from the slot to permit deployment of each clip through the slot by the actuator.

2. The catheter of claim 1, further comprising means for positioning a plurality of clips within said housing.

3. The catheter of claim 1, further comprising an inflatable member configured on the side wall of said housing so as to stabilize a position of said housing during deployment of a clip.

4. The catheter of claim 1, wherein said housing has an internal diameter in a range of about one to ten millimeters.

5. The catheter of claim 1, wherein said housing has an internal diameter of about two millimeters.

6. The catheter of claim 1, further comprising a flexible and torqueable portion having a proximal end and a distal end secured to the proximal end of said housing, wherein said housing is formed from a rigid material.

7. The catheter of claim 6, further comprising a handle secured to the proximal end of said flexible portion.

8. The catheter of claim 7, wherein the rigid material of said housing is stainless steel and said flexible portion is formed from a polyether block amide.

9. The catheter of claim 7, further comprising a lumen extending from the proximal end to the distal end of said flexible portion and from the proximal end to the distal end of said housing, said lumen having a proximal end in communication with an access port in said handle and having a distal opening proximate the distal end of said housing.

10. The catheter of claim 9, wherein said lumen is configured for a guidewire or introducer needle to be slidably disposed therein, such that the guidewire or needle locks the clip within said housing.

11. A delivery device for deploying a clip, the device comprising:

a housing having a distal end, a proximal end and a side wall, said housing having a slot formed proximate and proximal the distal end, wherein the slot is configured to provide deployment of a clip through the side wall; and means disposed within the housing for bending a clip from an open to a closed condition, the means comprising an actuator and an anvil movable independently of the clip and usable with a plurality of clips, the anvil being controllable to be positioned at the slot to bend each clip prior to deployment of the clip, and to be moved away from the slot to permit deployment of each clip through the slot by the actuator.

12. The delivery device of claim 11, further comprising means for positioning a plurality of clips within said housing.

13. The delivery device of claim 11, further comprising an inflatable member configured on the side wall of said housing so as to stabilize a position of said housing during deployment of a clip.

14. The delivery device of claim 11, wherein said housing has an internal diameter in a range of about one to ten millimeters.

15. The delivery device of claim 11, wherein said housing has an internal diameter of about two millimeters.

16. The delivery device of claim 11, wherein said means for bending includes means for retaining a clip and means for biasing a clip against the means for retaining.

17. The delivery device of claim 16, further comprising means for releasing a clip through the slot of said housing.

18. The delivery device of claim 17, wherein said means for releasing includes a slide wire connected to the anvil.

19. A delivery device for deploying a clip, the device comprising:

a housing having a distal end, a proximal end and a side wall, said housing having a slot formed proximate and proximal the distal end, wherein the slot is configured to provide deployment of a clip through the side wall;

means for releasing a clip through the slot of said housing; and means disposed within the housing for bending a clip from an open to a closed condition wherein said means for bending includes means for retaining a clip and means for biasing a clip against the means for retaining;

wherein the means for retaining includes an anvil, the anvil being controllable to be positioned at the slot prior to deployment of the clip, and said means for releasing includes a slide wire connected to the anvil; and wherein the means for biasing includes an actuator balloon and an actuator arm.

20. The delivery device of claim 19, wherein the means for biasing further includes an actuator tip positioned at a distal end of the actuator arm to engage a clip.

21. The delivery device of claim 20, further comprising an inflatable member configured on the side wall of said housing so as to stabilize a position of said housing during deployment of a clip.

22. The delivery device of claim 21, wherein the means for biasing further includes an inflation lumen in fluid communication with the actuator balloon and the inflatable member.

23. The delivery device of claim 21, further comprising a flexible and torqueable portion having a proximal end and a distal end secured to the proximal end of said housing, wherein said housing is formed from a rigid material.

24. The delivery device of claim 23, further comprising a handle secured to the proximal end of said flexible portion.

25. The delivery device of claim 17, wherein the means for retaining includes a shutter having an aperture and an anvil and said means for releasing includes a slide wire connected to the shutter.

26. The delivery device of claim 25, wherein the means for biasing includes a force wire slidably disposed in said housing, a force wedge connected to a distal end of the force wire and slidably disposed on the slide wire, and an actuator arm disposed within the force wedge, wherein distal translation of the force wire causes the actuator arm to engage and deploy a clip.

27. The delivery device of claim 26, wherein the means for biasing further includes an actuator tip positioned at a distal end of the actuator arm.

28. The delivery device of claim 17, wherein the means for retaining includes an anvil slidably disposed proximate the slot in said housing, and the means for biasing includes a force wire slidably disposed within a lumen having an opening proximate the anvil, the force wire having a first end movable by a user and a second end disposed proximate the anvil, and wherein distal translation of the force wire causes the second end to engage and deploy a clip.

29. The delivery device of claim 28, wherein the force wire and lumen are configured such that providing a tension force on the force wire causes the first end of the force wire to move proximate the anvil.

30. The delivery device of claim 28, wherein the force wire and lumen are configured such that providing a compression force on the force wire causes the first end of the force wire to move proximate the anvil.

31. The delivery device of claim 18, herein the means for biasing includes a force arm having a first end positioned proximate the anvil, an actuator arm movable by a user and at least one pivot connecting the actuator arm and the force arm.

32. A delivery device for deploying a clip into a valve of a vein, the device comprising:

a housing having a distal end, a proximal end and a side wall, said housing having a clip eject slot formed proximate and proximal the distal end, wherein the clip eject slot is configured to allow deployment of a clip through the side wall;

an anvil slidably disposed within said housing and positioned proximate the clip eject slot, said anvil configured to bend a clip;

an actuator arm disposed in said housing and having a distal end configured for engaging a clip; and an inflatable member disposed within said housing, wherein during inflation the inflatable member radially moves the distal end of said actuator arm proximate said anvil and the clip eject slot in said housing.

33. The delivery device of claim 32, further comprising a slide wire for sliding said anvil in a longitudinal direction within said housing.

34. The delivery device of claim 33, wherein the distal end of said actuator arm includes an actuator tip slidably disposed on said actuator arm.

35. The delivery device of claim 34, wherein the actuator tip includes an arcuate flange configured to engage a clip as recited in claim 3 so as to maximize penetration of the first and second legs of the clip into a target tissue, to enhance straightening of the third arcuate portion, and to maximize crossing of the first and second legs prior to releasing the clip from the housing.

36. The delivery device of claim 35, further comprising a flexible and torqueable portion having a proximal end and a distal end secured to the proximal end of said housing, wherein said housing is formed from a rigid material.

37. The delivery device of claim 36, further comprising a tapered tip having a conical distal end and a proximal end connected to the distal end of said housing and configured for positioning a clip proximate the clip eject slot.

38. The delivery device of claim 37, further comprising a handle secured to the proximal end of said flexible portion.

39. The delivery device of claim 38, wherein said housing has an internal diameter of about two millimeters.

40. The delivery device of claim 39, further comprising a lumen extending from the proximal end to the distal end of said flexible portion and from the proximal end to the distal end of said housing, said lumen having a proximal end in communication with an access port in said handle and having a distal opening proximate the distal end of said tapered tip.

41. The delivery device of claim 40, wherein said lumen is configured for a guidewire or introducer needle to be slidably disposed therein, such that the guidewire or needle releasably retains the clip within said housing.

42. In combination:

a clip having a first end and a second end, said clip including a first leg extending from the first end, a second leg extending from the second end, a first arcuate portion configured in the first leg, a second arcuate portion configured in the second leg and a middle arcuate portion configured between the first arcuate portion and the second arcuate portion, wherein the legs and arcuate portions form a "W" shape;

a catheter having a distal portion comprising a housing having a distal end, a proximal end and a side wall, the housing having a slot formed in the side wall proximate the distal end, wherein said clip is disposed in the housing proximate the slot and the slot is configured to allow release of said clip through the side wall; and means for deploying and bending said clip through the slot in the housing of said catheter, the means for deploying comprising an actuator and an anvil movable independently of the clip and reusable with a plurality of clips, the anvil being controllable to be positioned at the slot to shape each clip prior to deployment of the clip, and to be moved away from the slot to permit deployment of each clip through the slot by the actuator.

43. The combination of claim 42, further comprising means for positioning a plurality of clips within the housing of said catheter.

44. The combination of claim 42, further comprising an inflatable member configured on the side wall of the housing of said housing so as to stabilize a position of the housing during deployment of said clip.

45. The combination of claim 42, wherein said catheter further comprises a flexible and torqueable portion having a proximal end and a distal end secured to the proximal end of the housing, and the housing is formed from a rigid material.

46. The combination of claim 45, further comprising a handle secured to the proximal end of the flexible portion of said catheter.

47. The combination of claim 46, wherein said housing has an internal diameter of about two millimeters.

48. The combination of claim 42, wherein said housing has an internal diameter in a range of about one to ten millimeters.

49. The combination of claim 42, wherein the radius of each of the first arcuate portion, second arcuate portion and middle arcuate portion of said clip is about 0.01 inches.

50. The combination of claim 42, wherein said clip is configured such that the length of each of the first leg and the second leg is about 2.2 millimeters, the distance between a midpoint of the first arcuate portion and a midpoint of the second arcuate portion is about 1.9 millimeters, and the amplitude of the middle arcuate portion is about 0.8 millimeters.

51. The combination of claim 50, wherein the clip is configured from a wire-like material having a thickness in a range of about 0.002 to 0.006 inches.

52. The combination of claim 51, wherein the wire-like material is stainless steel.

53. An apparatus for deploying a clip into a valve of a vein, the apparatus comprising:

a clip having a first end and a second end, said clip including a first leg extending from the first end, a second leg extending from the second end, a first arcuate portion configured in the first leg, a second arcuate portion configured in the second leg and a middle arcuate portion configured between the first arcuate portion and the second arcuate portion;

a catheter having a proximal portion and a distal portion including a housing having a distal end, a proximal end and a side wall, a slot formed proximate and proximal the distal end of the housing, wherein said clip is positioned within said catheter and proximate the slot which is configured to allow said clip to release from said catheter through the side wall; and means disposed within the housing of said catheter for bending said clip from an open to a closed condition, the means comprising an actuator and an anvil movable independently of the clip and reusable with a plurality of clips, the anvil being controllable to be positioned at the slot to bend each clip prior to deployment of the clip, and to be moved away from the slot to permit deployment of each clip through the slot by the actuator.

54. The apparatus of claim 53, further comprising means for positioning a plurality of clips within the housing of said catheter.

55. The apparatus of claim 53, wherein said housing has an internal diameter in a range of about one to ten millimeters.

56. The apparatus of claim 53, wherein said housing has an internal diameter of about two millimeters.

57. The apparatus of claim 53, wherein said means for bending includes a retainer arm slidably disposed within the housing and having a distal end configured for engaging said clip, and said means for bending includes means for biasing said clip against the distal end of the retainer arm.

58. The apparatus of claim 57, wherein the distal end of the retainer arm includes the anvil configured for engaging the middle arcuate portion of said clip, and said means for bending further includes a slide wire connected to the retainer arm so as to position the anvil proximate the slot in the housing of said catheter.

59. An apparatus for deploying a clip into a valve of a vein, the apparatus comprising:

a clip having a first end and a second end, said clip including a first leg extending from the first end, a second leg extending from the second end, a first arcuate portion configured in the first leg, a second arcuate portion configured in the second leg and a middle arcuate portion configured between the first arcuate portion and the second arcuate portion;

a catheter having a proximal portion and a distal portion including a housing having a distal end, a proximal end and a side wall, a slot formed proximate and proximal the distal end of the housing, wherein said clip is positioned within said catheter and proximate the slot which is configured to allow said clip to release from said catheter through the side wall; and means disposed within the housing of said catheter for bending said clip from an open to a closed condition;

wherein said means for bending includes a retainer arm slidably disposed within the housing and having a distal end configured for engaging said clip, and said means for bending includes means for biasing said clip against the distal end of the retainer arm;

wherein the distal end of the retainer arm includes an anvil configured for engaging the middle arcuate portion of said clip, and said means for bending further includes a slide wire connected to the retainer arm so as to position the anvil proximate the slot in the housing of said catheter;

wherein the means for biasing comprises an actuator balloon and an actuator arm having a distal end movable by the actuator balloon to proximate the slot in the housing of said catheter.

60. The apparatus of claim 59, wherein the means for biasing further comprises an actuator tip disposed on the distal end of the actuator arm, the tip having an arcuate flange configured to engage said clip so as to maximize penetration of the first and second legs of said clip into a vein valve, to enhance straightening of the middle arcuate portion, and to maximize crossing of the first and second legs prior to releasing said clip from the housing.

61. The apparatus of claim 60, further comprising a delivery device configured on the side wall of the housing of said catheter so as to stabilize a position of said housing during deployment of a clip.

62. The apparatus of claim 61, further comprising means for inflating in fluid communication with the actuator balloon and the diverting balloon, such that the diverting balloon is fully inflated prior to full inflation of the actuator balloon.

63. The apparatus of claim 59, wherein said catheter further comprises a flexible and torqueable portion having a proximal end and a distal end secured to the proximal end of the housing, wherein the housing is formed from a rigid material.

64. The apparatus of claim 63, wherein said catheter further comprises a tapered tip having a conical distal end and a proximal end connected to the distal end of the housing.

65. The apparatus of claim 64, said catheter further comprises a handle secured to the proximal end of the flexible portion of said catheter.

66. The apparatus of claim 65, wherein said catheter further comprises a lumen extending from the proximal end to the distal end of the flexible portion and from the proximal end to the distal end of the housing, the lumen having a proximal end in communication with an access port in the handle and having a distal opening proximate the distal end of the tapered tip.

67. The apparatus of claim 66, further comprising a guidewire slidably disposed within the lumen of said catheter, such that the guidewire retains said clip within the housing.

68. The apparatus of claim 53, wherein the means for bending comprises:
   a shutter having an aperture and an anvil;
   a slide wire connected to the shutter;
   a force wire having a proximal end and a distal end and slidably disposed in said housing;
   a force wedge connected to the distal end of the force wire and slidably disposed on the slide wire; and
   an actuator arm disposed within the force wedge and having a distal end configured to engage said clip, wherein movement of the proximal end of the force wire in a longitudinal direction toward the distal end of the housing causes the actuator arm to move in a radial direction toward the slot in the housing so as to engage said clip.

69. The apparatus of claim 68, wherein the means for bending further includes an actuator tip positioned at the distal end of the actuator arm and configured for preferentially bending said clip.

70. The apparatus of claim 57, wherein the distal end of the retainer arm includes an anvil slidably positioned proximate the slot in the housing and configured for engaging the middle arcuate portion of said clip, and the means for biasing includes a force wire slidably disposed within a first lumen in the catheter and having an opening in communication with the slot, the force wire having a first end manipulated by a user and a second end movable through the slot in the housing, such that said clip is disposed in the lumen proximate the anvil and the second end of the force wire bends the clip around the anvil.

71. The apparatus of claim 70, wherein the force wire and first lumen are configured such that providing a tension force on the force wire causes said clip to bend around the anvil.

72. The apparatus of claim 70, wherein the force wire and first lumen are configured such that providing a compression force on the force wire causes said clip to bend around the anvil.

73. The apparatus of claim 70, wherein said catheter further comprises a second lumen extending from the proximal portion to the distal end of the housing, the second lumen configured for a guidewire or introducer needle to be slidably disposed therein.

74. The apparatus of claim 73, further comprising a guidewire slidably disposed within the second lumen of said catheter, such that the guidewire releasably retains said clip within the housing.

75. The apparatus as in claim 58, wherein said means for bending further comprises:
   a force arm having a first end, a bend and a second end so at to form an L-shape;
   an actuator tip slidably disposed on the second end of the force arm;
   a first pivot secured to the housing and rotatably disposed within the bend of the force arm;
   a second pivot secured to the first end of said force arm; and
   a force actuator having a first end and a second end slidably disposed within the housing and rotatably secured to the second pivot, wherein movement of the first end of the force actuator in a longitudinal direction toward the distal end of the housing causes the actuator tip to move in a radial direction toward the slot in the housing so as to engage said clip.

76. The apparatus of claim 75, wherein said catheter further comprises a tapered tip having a conical distal end and a proximal end connected to the distal end of the housing, the tapered tip having a guidewire lumen configured from the proximal end to the distal end.

77. A method for deploying a clip within a vein valve, the method comprising:
   inserting a catheter having a distal portion into a vein of a patient, the distal portion of the catheter comprising a housing having a proximal end and a distal end configured with a clip eject slot positioned proximate and proximal the distal end;
   positioning the housing of the catheter proximate a vein valve having a wall;
   aligning the clip eject slot of the housing proximate a commissure of the vein valve;
   manipulating a clip within the housing to position the clip proximate the eject slot;
   sliding an anvil, separate from the clip, that is disposed within the housing of the catheter to a position proximate the clip eject slot, wherein the anvil is independently movable in relation to the clip and is configured to bend the clip;
   bending the clip around the anvil;
   sliding the anvil to a position other than at the slot prior to releasing the clip from the slot in the housing;
   applying force to the clip to pierce the vein valve and wall so as to secure the clip thereto;
   releasing the clip from the housing through the eject slot; and removing the catheter from the vein.

78. The method of claim 77, wherein said applying force to the clip step includes inflating a balloon against an actuator arm so as to engage the actuator arm with the clip.

79. The method of claim 78, further including the steps of providing a clip as recited in claim 3, and engaging the clip with a sliding actuator tip configured on a distal end of the actuator arm so as to maximize penetration of the first and second legs of the clip into the vein valve, to enhance straightening of the third arcuate portion, and to maximize crossing of the first and second legs prior to releasing the clip from the housing.

80. The method of claim 79, further including the steps of inflating a diverting balloon configured on an outside wall of the housing of the catheter, and moving the housing in close proximity with the commissure of the vein valve so as to stabilize the housing while releasing the clip from the housing.

81. The method of claim 78, further including the steps of providing a clip as recited in claim 27, and engaging the clip with a sliding actuator tip configured on a distal end of the actuator arm so as to maximize penetration of the first and second legs of the clip into the vein valve, to enhance straightening of the third arcuate portion, and to maximize crossing of the first and second legs prior to releasing the clip from the housing.

82. The method of claim 77, further comprising the step of providing a shutter configured with an aperture and the anvil, a slide wire connected to the shutter, a force wire having a proximal end and a distal end, a force wedge connected to the distal end of the force wire and slidably disposed on the slide wire, and an actuator arm disposed within the force wedge; and
wherein said applying force to the clip step includes moving the proximal end of the force wire in a longitudinal direction toward the distal end of the housing so as to move the distal end of the actuator arm in a radial direction toward the slot in the housing so as to engage the clip.

83. The method of claim 77, wherein the catheter further comprises a force wire slidably disposed within a lumen in the catheter, the lumen having an opening in communication with the eject slot such that the clip is disposed in the lumen proximate the anvil, the force wire having a proximal end movable by a user and a distal end positioned to engage the clip; and
wherein said applying force to the clip step includes moving the force wire longitudinally in the lumen so as to engage the distal end of the force wire with the clip and push the clip against the anvil.

84. The method of claim 83, wherein said moving the force wire longitudinally step includes applying a tension force on the force wire.

85. The method of claim 83, wherein said moving the force wire longitudinally step includes applying a compression force on the force wire.

86. The method of claim 77, wherein the catheter further comprises a force arm rotatably disposed within the housing and having a proximal end and a distal end disposed proximate the clip eject slot, a force actuator slidably disposed within the housing and having a proximal end and a distal end, and at least one pivot rotatably connecting the distal end of the force actuator to the proximal end of the force arm; and
wherein said applying force to the clip step includes moving the proximal end of the force actuator in a longitudinal direction toward the distal end of the housing so as to move the distal end of the force arm in a radial direction toward the slot in the housing so as to engage the clip and force the clip against the anvil.

87. A method for deploying a clip within a body lumen or cavity of a patient, the method comprising:
inserting into a patient a catheter having a distal portion comprising a housing having a proximal end and a distal end configured with a clip eject slot positioned proximate and proximal the distal end;
positioning the housing of the catheter proximate a desired location in the patient;
aligning the clip eject slot of the housing proximate the desired location in the patient;
manipulating a clip within the housing to position the clip proximate the eject slot;
sliding an anvil that is disposed within the housing of the catheter to a position proximate the clip eject slot, wherein the anvil is independently movable in relation to the clip and is configured to bend the clip;
bending the clip around the anvil;
positioning the anvil to a position other than at the slot prior to releasing the clip from the slot in the housing;
applying force to the clip to secure the clip to the desired location in a patient;
releasing the clip from the housing through the eject slot; and
removing the catheter from the patient.

88. The method of claim 87, further including the steps of expanding an inflatable member configured on an outside wall of the housing of the catheter, and moving the housing in close proximity with the commissure of the vein valve so as to stabilize the housing while releasing the clip from the housing.

89. A method for deploying a clip within a blood vessel, the method comprising:
(a) providing a catheter having a distal portion comprising a housing having a distal end configured with a clip eject slot positioned proximate and proximal the distal end, the catheter further having an anvil slidably disposed within the housing and at least one clip positioned proximate the anvil and the eject slot, the anvil being independently movable in relation to the clip and reusable with a plurality of separate clips;
(b) inserting the distal portion of the catheter into a blood vessel of a patient;
(c) positioning the housing of the catheter proximate a desired location in the blood vessel;
(d) aligning the clip eject slot of the housing proximate the desired location in the blood vessel;
(e) positioning the anvil proximate the clip eject slot in the housing, wherein the anvil is configured to bend the clip;
(f) applying force to the clip to push the clip against the anvil and to engage the clip with the blood vessel;
(g) bending the clip around the anvil and into the blood vessel;
(h) positioning the anvil to a location removed from the eject slot prior to releasing the clip through the eject slot in the housing;
(i) releasing the clip from the housing through the eject slot; and
(j) removing the catheter from the blood vessel.

90. The method of claim 89, wherein said providing a catheter step includes providing a plurality of clips in the housing of the catheter, and further comprising repeating steps (c) through (i) prior to completing step (j).

91. The method of claim 89, further including the steps of expanding an inflatable member configured on an outside wall of the housing of the catheter, and moving the housing in close proximity with the commissure of the vein valve so as to stabilize the housing while releasing the clip from the housing.

92. The method of claim 89, wherein the blood vessel is a vein, said positioning the housing step includes positioning the housing superior a valve in a vein, and said aligning the clip eject slot step includes aligning the eject slot superior to a commissure of the valve.

93. A method for repairing an incompetent vein valve, the method comprising:
- (a) providing a catheter having a distal portion comprising a housing having a distal end configured with a clip eject slot positioned proximate and proximal the distal end, the catheter further having an anvil slidably disposed within the housing and a plurality of clips positioned proximate the anvil and the eject slot, the anvil being independently movable in relation to the clip and reusable with a plurality of separate clips;
- (b) inserting the distal portion of the catheter into a vein of a patient;
- (c) positioning the housing of the catheter proximate an incompetent valve in the vein;
- (d) aligning the clip eject slot of the housing proximate the vein valve;
- (e) positioning the anvil proximate the clip eject slot in the housing, wherein the anvil is configured to bend a clip;
- (f) applying force to a clip to push the clip against the anvil and to engage the clip with a wall of the valve;
- (g) bending the clip around the anvil and through the wall of the valve;
- (h) positioning the anvil to a location removed from the eject slot prior to releasing the clip through the eject slot in the housing;
- (i) releasing the clip from the housing through the eject slot; and
- (j) removing the catheter from the vein.

94. The method of claim 93, wherein said step (c) includes positioning the housing proximate a first incompetent valve, and said step (d) includes aligning the eject slot proximate a first commissure of the valve.

95. The method of claim 94, further comprising, after step (i) and prior to performing step (j), repositioning the eject slot adjacent the clip released in step (i) and proximate the first commissure, and repeating steps (e) through (i) prior to completing step (j).

96. The method of claim 94, further comprising, after step (i) and prior to performing step (j), aligning the eject slot proximate a second commissure in the first incompetent valve, and repeating steps (e) through (i).

97. The method of claim 94, further comprising after step (i) and prior to completing step (j) positioning the housing proximate a second incompetent valve, aligning the eject slot proximate a commissure of the second incompetent valve, and repeating steps (e) through (i).

98. The method of claim 94, further comprising, after step (i) and prior to performing step (j), aligning the eject slot proximate a second commissure in the first vein valve, and repeating steps (e) through (i).

99. The method of claim 93, further comprising after step (i) and prior to completing step (j) positioning the housing proximate a second vein valve, aligning the eject slot proximate a commissure of the second vein valve, and repeating steps (e) through (i).

100. The method of claim 93, after step (d) and before step (f), further including the steps of expanding an inflatable member configured on an outside wall of the housing of the catheter, and moving the housing in close proximity with the commissure of the vein valve so as to stabilize the housing while releasing the clip from the housing.

101. The method of claim 94, after step (f), further including the steps of expanding an inflatable member configured on an outside wall of the housing of the catheter so as to engage the clip with a first and a second leaflet of the incompetent vein valve, and moving the housing in close proximity with the commissure of the vein valve so as to stabilize the housing while releasing the clip from the housing.

102. A method of restoring the competency of a vein valve by reducing the diameter of the vein, the method comprising the steps of:
- inserting a catheter in the vein, the catheter having a housing and a clip eject slot formed in the housing;
- positioning the clip eject slot adjacent the vein valve;
- manipulating a clip within the housing to position the clip in the clip eject slot;
- moving an anvil to the clip eject slot, the anvil being movable independently of the clip and reusable with a plurality of clips;
- shaping the clip with the anvil prior to deployment of the clip;
- moving the anvil away from the slot to permit deployment of the clip through the slot; and
- applying force to the clip to engage the vein wall adjacent the vein valve so as to reduce the diameter of the vein wherein the clip is released from the slot in the housing.

103. The method of claim 102, further comprising the steps of:
- disposing an anvil slidably within the housing of the catheter, wherein the anvil is configured to bend the clip;
- positioning the anvil proximate the clip eject slot in the housing;
- bending the clip around the anvil; and
- positioning the anvil so that the clip is released from the slot in the housing.

104. The method of claim 102, further comprising the step of providing a shutter configured with an aperture and an anvil, a slide wire connected to the shutter, a force wire having a proximal end and a distal end, a force wedge connected to the distal end of the force wire and slidably disposed on the slide wire, and an actuator arm disposed within the force wedge; and
- wherein said step of applying force to the clip includes moving the proximal end of the force wire in a longitudinal direction toward the distal end of the housing so as to move the distal end of the actuator arm in a radial direction toward the slot in the housing so as to engage the clip.

105. The method of claim 102, further comprising the step of inflating a diverting balloon on the housing to stabilize the housing in the vein.

106. A catheter for deploying a clip appliance, the catheter comprising:
- a housing having a distal end, a proximal end and a side wall, said housing having a slot formed proximate the distal end, wherein the slot is configured to provide deployment of a clip through the side wall;

means for deploying a clip through the slot in the side wall of said housing; and an inflatable member configured on the side wall of said housing so as to stabilize a position of said housing during deployment of a clip.

107. A delivery device for deploying a clip, the device comprising:

a housing having a distal end, a proximal end and a side wall, said housing having a slot formed proximate and proximal the distal end, wherein the slot is configured to provide deployment of a clip through the side wall;

means disposed within the housing for bending a clip from an open to a closed condition; and an inflatable member configured on the side wall of said housing so as to stabilize a position of said housing during deployment of a clip.

108. In combination:

a clip having a first end and a second end, said clip including a first leg extending from the first end, a second leg extending from the second end, a first arcuate portion configured in the first leg, a second arcuate portion configured in the second leg and a middle arcuate portion configured between the first arcuate portion and the second arcuate portion, wherein the legs and arcuate portions form a "W" shape;

a catheter having a distal portion comprising a housing having a distal end, a proximal end and a side wall, the housing having a slot formed in the side wall proximate the distal end, wherein said clip is disposed in the housing proximate the slot and the slot is configured to allow release of said clip through the side wall;

means for deploying and bending said clip through the slot in the housing of said catheter; and an inflatable member configured on the side wall of the housing of said housing so as to stabilize a position of the housing during deployment of said clip.

109. An apparatus for deploying a clip into a valve of a vein, the apparatus comprising:

a clip having a first end and a second end, said clip including a first leg extending from the first end, a second leg extending from the second end, a first arcuate portion configured in the first leg, a second arcuate portion configured in the second leg and a middle arcuate portion configured between the first arcuate portion and the second arcuate portion;

a catheter having a proximal portion and a distal portion including a housing having a distal end, a proximal end and a side wall, a slot formed proximate and proximal the distal end of the housing, wherein said clip is positioned within said catheter and proximate the slot which is configured to allow said clip to release from said catheter through the side wall; and means disposed within the housing of said catheter for bending said clip from an open to a closed condition;

wherein said means for bending includes a retainer arm slidably disposed within the housing and having a distal end configured for engaging said clip, and said means for bending includes means for biasing said clip against the distal end of the retainer arm;

wherein the distal end of the retainer arm includes an anvil configured for engaging the middle arcuate portion of said clip, and said means for bending further includes a slide wire connected to the retainer arm so as to position the anvil proximate the slot in the housing of said catheter; and wherein the means for biasing comprises an actuator balloon and an actuator arm having a distal end movable by the actuator balloon to proximate the slot in the housing of said catheter.

110. A method for deploying a clip within a vein valve, the method comprising:

inserting a catheter having a distal portion into a vein of a patient, the distal portion of the catheter comprising a housing having a proximal end and a distal end configured with a clip eject slot positioned proximate and proximal the distal end;

positioning the housing of the catheter proximate a vein valve having a wall;

aligning the clip eject slot of the housing proximate a commissure of the vein valve;

manipulating a clip within the housing to position the clip proximate the eject slot;

providing an anvil slidably disposed within the housing of the catheter, wherein the anvil is configured to bend the clip;

positioning the anvil proximate the clip eject slot in the housing;

bending the clip around the anvil;

positioning the anvil so that the clip may be released from the slot in the housing;

applying force to the clip to pierce the vein valve and wall so as to secure the clip thereto;

releasing the clip from the housing through the eject slot; and removing the catheter from the vein valve and vein;

wherein said applying force to the clip step includes inflating a balloon against an actuator arm so as to engage the actuator arm with the clip.

111. A method for deploying a clip within a body lumen or cavity of a patient, the method comprising:

inserting into a patient a catheter having a distal portion comprising a housing having a proximal end and a distal end configured with a clip eject slot positioned proximate and proximal the distal end;

positioning the housing of the catheter proximate a desired location in the patient;

aligning the clip eject slot of the housing proximate the desired location in the patient;

manipulating a clip within the housing to position the clip proximate the eject slot;

providing an anvil slidably disposed within the housing of the catheter, wherein the anvil is configured to bend the clip;

positioning the anvil proximate the clip eject slot in the housing;

bending the clip around the anvil; and positioning the anvil so that the clip may be released from the slot in the housing;

applying force to the clip to secure the clip to the desired location in a patient;

releasing the clip from the housing through the eject slot;

expanding an inflatable member configured on an outside wall of the housing of the catheter, and moving the housing in close proximity with the commissure of the vein valve so as to stabilize the housing while releasing the clip from the housing; and removing the catheter from the patient.

112. A method for deploying a clip within a blood vessel, the method comprising:

(a) providing a catheter having a distal portion comprising a housing having a distal end configured with a clip eject slot positioned proximate and proximal the distal end, the catheter further having an anvil slidably disposed within the housing and at least one clip positioned proximate the anvil and the eject slot;

(b) inserting the distal portion of the catheter into a blood vessel of a patient;

(c) positioning the housing of the catheter proximate a desired location in the blood vessel;

(d) aligning the clip eject slot of the housing proximate the desired location in the blood vessel;

(e) positioning the anvil proximate the clip eject slot in the housing, wherein the anvil is configured to bend the clip;

(f) applying force to the clip to push the clip against the anvil and to engage the clip with the blood vessel;

(g) bending the clip around the anvil and into the blood vessel;

(h) positioning the anvil so that the clip may be released through the eject slot in the housing;

(i) expanding an inflatable member configured on an outside wall of the housing of the catheter, and moving the housing in close proximity with the commissure of the vein valve so as to stabilize the housing while releasing the clip from the housing;

(j) releasing the clip from the housing through the eject slot; and (k) removing the catheter from the blood vessel.

113. A method for repairing an incompetent vein valve, the method comprising:

(a) providing a catheter having a distal portion comprising a housing having a distal end configured with a clip eject slot positioned proximate and proximal the distal end, the catheter further having an anvil slidably disposed within the housing and a plurality of clips positioned proximate the anvil and the eject slot;

(b) inserting the distal portion of the catheter into a vein of a patient;

(c) positioning the housing of the catheter proximate an incompetent valve in the vein;

(d) aligning the clip eject slot of the housing proximate the vein valve;

(e) positioning the anvil proximate the clip eject slot in the housing, wherein the anvil is configured to bend a clip;

(f) expanding an inflatable member configured on an outside wall of the housing of the catheter;

(g) moving the housing in close proximity with the commissure of the vein valve so as to stabilize the housing while releasing the clip from the housing;

(h) applying force to a clip to push the clip against the anvil and to engage the clip with a wall of the valve;

(i) bending the clip around the anvil and through the wall of the valve;

(j) positioning the anvil so that the clip may be released through the eject slot in the housing;

(k) releasing the clip from the housing through the eject slot; and (l) removing the catheter from the vein.

114. A method for repairing an incompetent vein valve, the method comprising:

(a) providing a catheter having a distal portion comprising a housing having a distal end configured with a clip eject slot positioned proximate and proximal the distal end, the catheter further having an anvil slidably disposed within the housing and a plurality of clips positioned proximate the anvil and the eject slot;

(b) inserting the distal portion of the catheter into a vein of a patient;

(c) positioning the housing of the catheter proximate an incompetent valve in the vein and positioning the housing proximate a first incompetent valve;

(d) aligning the clip eject slot of the housing proximate the vein valve and aligning the eject slot proximate a first commissure of the valve;

(e) positioning the anvil proximate the clip eject slot in the housing, wherein the anvil is configured to bend a clip;

(f) applying force to a clip to push the clip against the anvil and to engage the clip with a wall of the valve;

(g) bending the clip around the anvil and through the wall of the valve;

(h) positioning the anvil so that the clip may be released through the eject slot in the housing;

(i) expanding an inflatable member configured on an outside wall of the housing of the catheter so as to engage the clip with a first and a second leaflet of the incompetent vein valve;

(j) moving the housing in close proximity with the commissure of the vein valve so as to stabilize the housing while releasing the clip from the housing;

(k) releasing the clip from the housing through the eject slot; and (l) removing the catheter from the vein.

* * * * *

UNITED STATES PATENT AND TRADEMARK OFFICE
CERTIFICATE OF CORRECTION

PATENT NO. : 6,149,660
DATED : November 21, 2000
INVENTOR(S) : Michael D. Laufer et al.

It is certified that error appears in the above-identified patent and that said Letters Patent is hereby corrected as shown below:

<u>Title page,</u>
Item [56], References Cited,
U.S. PATENT DOCUMENTS, add the following:

| | | |
|---|---|---|
| -- 4,509,618 | 4/1985 | McGary |
| 3,867,944 | 2/1975 | Samuels |
| 3,825,009 | 5/1973 | Williams |
| 3,735,762 | 5/1973 | Bryan, et al. |
| 3,643,851 | 2/1972 | Green, et al. |
| 3,584,628 | 6/1971 | Green |
| 3,545,944 | 12/1970 | Green |
| 3,120,230 | 2/1964 | Skold |
| 2,236,581 | 4/1941 | Schenck --. |

FOREIGN PATENT DOCUMENTS, add the following:
-- SU 1364322  7/1998  Soviet Union --.

<u>Column 29,</u>
Line 20, after "clip", delete "as recited in claim 27".

Signed and Sealed this

First Day of October, 2002

*Attest:*

*Attesting Officer*

JAMES E. ROGAN
*Director of the United States Patent and Trademark Office*